(12) United States Patent
Ralph et al.

(10) Patent No.: US 8,460,346 B2
(45) Date of Patent: *Jun. 11, 2013

(54) CRANIOTOMY CLOSURES

(75) Inventors: James D. Ralph, Bethlehem, PA (US);
Thomas N. Troxell, Pottstown, PA (US);
Mark Michels, Glen Mills, PA (US)

(73) Assignee: BioDynamics LLC, Englewood, NJ (US)

( * ) Notice: Subject to any disclaimer, the term of this patent is extended or adjusted under 35 U.S.C. 154(b) by 278 days.

This patent is subject to a terminal disclaimer.

(21) Appl. No.: 12/249,005

(22) Filed: Oct. 10, 2008

(65) Prior Publication Data
US 2009/0076617 A1    Mar. 19, 2009

Related U.S. Application Data

(63) Continuation-in-part of application No. 11/333,102, filed on Jan. 17, 2006, now Pat. No. 7,833,253.

(51) Int. Cl.
*A61B 17/80* (2006.01)
(52) U.S. Cl.
USPC .......... 606/284; 606/300; 623/17.19
(58) Field of Classification Search
USPC . 606/60, 70, 71, 283–286; 403/397; 277/637, 277/640, 647, 598; 600/206–208; 623/17.17–19.19, 16.11, 23.63; 248/230.8, 248/230.9; 433/172, 173, 193; 132/53, 54
See application file for complete search history.

(56) References Cited

U.S. PATENT DOCUMENTS

| 986,543 A | 3/1911 | Burroughes |
| 1,105,105 A | 7/1914 | Sherman |
| 1,278,133 A | 9/1918 | Gammeter |
| 2,543,963 A | 3/1951 | Gaffin |
| 2,626,164 A | 1/1953 | West |
| 2,706,023 A | 4/1955 | Merritt |
| 2,795,387 A | 6/1957 | McNeely |
| 4,309,120 A | 1/1982 | Werthmann |
| 4,323,217 A | 4/1982 | Dochterman |
| 4,683,878 A | 8/1987 | Carter |
| 4,726,808 A | 2/1988 | Collins |
| 4,746,129 A | 5/1988 | Puccio |
| 4,805,270 A * | 2/1989 | Kimbrough ............ 24/712.3 |
| 4,966,599 A | 10/1990 | Pollock |

(Continued)

FOREIGN PATENT DOCUMENTS

| EP | 1437098 | 7/2004 |
| EP | 1437098 | 8/2006 |
| WO | WO 9007304 | 7/1990 |

OTHER PUBLICATIONS

U.S. Appl. No. 11/025,213, filed Dec. 29, 2004, Ralph.

(Continued)

*Primary Examiner* — Ellen C Hammond
(74) *Attorney, Agent, or Firm* — Lowenstein Sandler LLP

(57) ABSTRACT

Craniotomy closures comprising surgical fasteners are described for use in reattaching a skull flap removed from the skull of a patient during brain surgery. Methods of using the same are also described. Surgical strips used in combination with the fasteners are shaped to follow the perimeter contour of the skull flap. The craniotomy closures are designed to encourage bone growth and healing of the skull flap and they can be used to deliver medication and bone growth enhancement materials to the surgical site.

7 Claims, 20 Drawing Sheets

U.S. PATENT DOCUMENTS

| | | | |
|---|---|---|---|
| 5,047,047 A | | 9/1991 | Yoon |
| 5,099,552 A | * | 3/1992 | Kimbrough .................. 24/715.6 |
| 5,413,577 A | | 5/1995 | Pollock |
| 5,503,164 A | | 4/1996 | Friedman |
| 5,571,105 A | * | 11/1996 | Gundolf .......................... 606/74 |
| 5,649,927 A | * | 7/1997 | Kilpela et al. .................. 606/74 |
| 5,669,912 A | | 9/1997 | Spetzler |
| 5,707,373 A | | 1/1998 | Sevrain et al. |
| 5,730,743 A | | 3/1998 | Kirsch et al. |
| 5,752,958 A | | 5/1998 | Wellisz |
| 5,797,915 A | | 8/1998 | Pierson et al. |
| 5,814,048 A | | 9/1998 | Morgan |
| 6,022,351 A | | 2/2000 | Bremer et al. |
| 6,050,998 A | * | 4/2000 | Fletcher .......................... 606/74 |
| 6,068,631 A | | 5/2000 | Lerch |
| 6,102,347 A | * | 8/2000 | Benoit ....................... 248/230.8 |
| 6,190,389 B1 | | 2/2001 | Wellisz et al. |
| 6,197,037 B1 | | 3/2001 | Hair |
| 6,258,091 B1 | | 7/2001 | Servain et al. |
| 6,325,803 B1 | | 12/2001 | Schumacher et al. |
| 6,328,743 B2 | | 12/2001 | Lerch |
| 6,350,284 B1 | | 2/2002 | Tormala et al. |
| 6,355,044 B1 | * | 3/2002 | Hair .............................. 606/326 |
| 6,364,881 B1 | | 4/2002 | Apgar et al. |
| 6,511,482 B1 | | 1/2003 | Wellisz et al. |
| 6,554,835 B1 | | 4/2003 | Lee |
| 6,572,623 B1 | * | 6/2003 | Birchall et al. ................. 606/76 |
| 6,582,435 B2 | | 6/2003 | Wellisz et al. |
| 6,589,244 B1 | | 7/2003 | Servain et al. |
| 6,641,588 B2 | | 11/2003 | Citron et al. |
| 6,652,531 B2 | | 11/2003 | Wellisz et al. |
| 6,682,533 B1 | | 1/2004 | Dinsdale et al. |
| 6,692,498 B1 | | 2/2004 | Niiranen et al. |
| 6,776,800 B2 | * | 8/2004 | Boyer et al. ............... 623/23.63 |
| 6,821,279 B2 | | 11/2004 | Di Emidio |
| 6,855,169 B2 | | 2/2005 | Boyer et al. |
| 6,921,401 B2 | | 7/2005 | Lerch et al. |
| 7,090,459 B2 | | 8/2006 | Bhate et al. |
| 7,168,569 B2 | | 1/2007 | Peresan |
| 7,182,785 B2 | | 2/2007 | Elsalanty et al. |
| 2002/0040242 A1 | | 4/2002 | Picha et al. |
| 2002/0062127 A1 | | 5/2002 | Schumacher et al. |
| 2002/0120338 A1 | * | 8/2002 | Boyer et al. ............... 623/17.19 |
| 2003/0100901 A1 | | 5/2003 | Wellisz et al. |
| 2003/0229349 A1 | | 12/2003 | Wellisz et al. |
| 2004/0034375 A1 | | 2/2004 | Ruiz et al. |
| 2004/0138591 A1 | | 7/2004 | Iseki et al. |
| 2004/0153125 A1 | | 8/2004 | Roby |
| 2004/0210224 A1 | | 10/2004 | Ahmad et al. |
| 2005/0033425 A1 | | 2/2005 | Schwab |
| 2005/0090831 A1 | | 4/2005 | Ahmad et al. |
| 2005/0240189 A1 | | 10/2005 | Rosseau et al. |
| 2006/0229610 A1 | | 10/2006 | Piehl |
| 2006/0285918 A1 | | 12/2006 | Legat et al. |
| 2008/0071323 A1 | | 3/2008 | Lowry et al. |
| 2008/0077133 A1 | | 3/2008 | Schulze |
| 2010/0179553 A1 | | 7/2010 | Ralph et al. |
| 2010/0179554 A1 | | 7/2010 | Ralph et al. |
| 2011/0054540 A1 | | 3/2011 | Ralph et al. |

OTHER PUBLICATIONS

U.S. Appl. No. 11/333,102, filed Jan. 17, 2006, Ralph.
Partial European Search Report, Aug. 22, 2006.
International Search Report, May 25, 2007.
Steller Technical Products, Lead-Free CAme, 2004, http://www.stellartechnical.com/csg3.html.
U.S. Appl. No. 12/710,614(US 2010-0179554) OA dated Apr. 6, 2011.
U.S. Appl. No. 12/710,614(US 2010-0179554) Response dated Jul. 6, 2011.
U.S. Appl. No. 12/710,541 (US 2010-0179553) OA dated Apr. 6, 2011.
U.S. Appl. No. 12/710,541 (US 2010-0179553) Response dated Jul. 6, 2011.
U.S. Appl. No. 12/942,444 (US 2011-0054540) OA dated May 13, 2011.

* cited by examiner

CRANIOTOMY CLOSURES

CROSS-REFERENCE TO RELATED APPLICATION

This application is a continuation-in-part of Ser. No. 11/333,102 filed Jan. 17, 2006 now U.S. Pat. No. 7,833,253.

FIELD OF THE INVENTION

The invention relates to surgical fasteners, particularly for use in reattaching a skull flap removed during brain surgery and methods of reattaching the skull flap using the fasteners. In further aspects, the invention relates to a surgical strip used in combination with the fasteners, methods of implanting the fasteners and strips of the invention and methods which enhance bone growth and the consequent healing of the skull flap and the skull.

BACKGROUND OF THE INVENTION

Surgical access to the brain for neurosurgical procedures is created by removing a portion of the patient's skull to provide an exposed area of soft tissue of the brain for surgery, a procedure termed a craniotomy. The craniotomy is determined by the location of the pathology within the brain, the safest/easiest access route and the degree of exposure required for the procedure. Once the location is determined, the first step is to create an initial perforation of the full thickness of the skull. Special skull perforators are available to create perfectly round holes but most surgeons simply use a rounded, end-cutting burr to create the perforation. Typically the perforation is in the range of about 11-15 millimeters (mm) in diameter. A surgeon may choose to create more than one perforation around the perimeter of the planned craniotomy. Some surgeons prefer a single perforation and others use more than one, but there is no standard number. Once this hole is created, it allows the insertion of a rotary powered surgical instrument (e.g., a craniotome) which is used to create a continuous cut (also called an osteotomy cut or a kerf) around the perimeter of the craniotomy. This kerf begins and ends at the perforation when there is one perforation or it runs from one perforation to another when more than one perforation is made in the skull. The kerf is made with a side cutting burr which is shielded from the dura (outer covering of the brain) by a foot plate on the craniotome. The foot plate extends below and forward of the cutting burr and the surgeon keeps the tip of the foot plate in contact with the inner surface of the skull as he performs the craniotomy. The typical kerf is made freehand with an approximately 2 mm diameter burr. The shape of the craniotomy is therefore highly variable and the kerf is not always oriented perpendicular to the skull. The kerf may be larger than 2 mm in some areas as well. Over the course of the kerf, the skull thickness will vary, typically over the range of 3-8 mm in adults.

Once the cut is complete, the skull flap is removed from the skull and placed on the sterile back table for reinsertion at the end of the procedure. After completion of the soft tissue surgery (typically 1-6 hours), the skull flap is inserted back into the craniotomy and fixated to prevent movement and restore the original contour of the skull. The surgeon may bias the skull flap toward one side or another to create bone-to-bone contact in a particular area or he may leave a gap around the entire flap. The scalp is then closed and the patient is sent to the neurosurgical intensive care unit for recovery.

If complications develop while the patient is in the hospital, there may be the need for emergency access to the brain through the craniotomy site. In addition, some patients may return for subsequent craniotomies in the same region, particularly in cases of recurrent tumors. Postoperative imaging studies (MRI or CT) are generally conducted on all patients. There is no clear evidence that the skull flap ever completely heals (solid bony union) in adults. It is more likely that a combination of new bone formation and fibrous connective tissue fills the gap between the skull and the skull flap.

From a surgeon's perspective, the method of reattaching the bone flap must be safe, simple to use, be rapidly applied, permit emergent re-entry, not interfere with postoperative imaging studies, provide stable fixation and have an acceptably low profile. The ideal method would result in complete fusion of the bone flap to the native skull with no long term evidence of prior surgery.

Current methods of reattaching the skull flap include drilling a series of small holes in the edge of the skull and the edge of the flap. Sutures are then passed through the corresponding holes and the flap is secured back into the skull opening from which it was taken. Because the fit is not exact due to the material removed by the craniotome, the flap can sag and sit slightly below the surface of the skull resulting in a depressed area that is obvious through the skin.

Another common reattachment method substitutes stainless steel wire for the suture material and fewer holes are used. There is still the risk of a cosmetically objectionable depressed area resulting. Metallic cranial fixation is (generally) only ever removed if it becomes symptomatic or if it interferes with subsequent surgeries.

More recently, surgeons have begun to use the titanium micro plates and screws that were developed for internal fixation of facial and finger bones. While this method results in a more stable and cosmetic result, it is relatively expensive, does not insure fusion and leaves foreign bodies at the surgical site.

All of these methods take ten minutes to one hour of additional surgery after the soft tissue (brain) surgery.

There is another method in which a titanium rivet (or clamp) is placed inside the skull with the stem of the rivet (clamp) passing between the skull and the flap. A large "pop rivet" type tool is used to force an upper titanium button down over the stem of the rivet, locking the flap and the skull in place between the upper and lower buttons. Three or four of these rivets and buttons are used to secure the flap in place. This method can be faster than other methods and less expensive than the titanium plates, but more expensive than sutures or wires. Just as with titanium plates and screws, fusion is not assured and foreign bodies remain in the patient.

According to the present invention we have developed new surgical fasteners for, and methods of, reattaching a skull flap in a skull opening. The fixation provided utilizing a fastener of the invention and practicing the methods of the invention is secure and cosmetically acceptable. The fastener is used in combination with materials which can enhance bone growth in a manner which causes healing by means of bone-to-bone reattachment of the skull flap to the skull.

The term "perimeter contour" as used herein with reference to the skull flap means "the shape of the outer boundary around the skull flap."

The term "shaped to follow the perimeter contour" means "formed around the perimeter contour."

SUMMARY OF THE INVENTION

The surgical fasteners of the present invention allow the surgeon to reattach the skull flap in generally the same position from which it was removed, thereby maintaining the contour of the skull in a manner which is cosmetically desirable. The fasteners also position the flap in the skull in a manner which provides a generally even gap (the kerf) between the flap and the skull around the perimeter of the flap. Flexible surgical strips used in combination with the surgical fasteners can be shaped to follow the perimeter contour of the skull flap and, consequently, the contour of the opening in the skull from which the flap was removed. These strips are placed or implanted in the kerf between the flap and the skull. In a preferred embodiment, a craniotomy closure of the invention is comprised of at least two fasteners, used to reattach the skull flap, and one or more than one surgical strip.

The fastener comprises a flange which is disposed over and adjacent to the skull flap and the skull. A projection extends from the underside of the flange. The projection extends into the kerf and acts as a spacer between the skull flap and the skull to make the generally even gap. In some embodiments, the projection can be flexible and somewhat wider than the kerf to make a snug fit. But the flexibility of the projection should be somewhat limited so that the function of the projection to act as a spacer is not compromised.

A strip or ribbon of material can comprise the element of the surgical strip which is shaped to follow the perimeter contour of the skull flap. Some embodiments of the surgical strip are provided with one or more cavities disposed along its length. The cavities generally are located in the strip so that they are disposed between the skull flap and the skull when the strip is implanted in a patient. For example, the cavity may have a uniform cross section along the entire length of the strip such as in the shape of a U, V, J, W or pleats or corrugations or it may be a closed tube or a solid having the cross-sectional shape of a circle, oval, ellipse, square, rectangle, triangle or any other closed geometric shape.

The strip can also be a moldable material which may be, for example, in the form of a putty, paste or gel (i.e., a putty-like, paste-like or gel-like material) or a compressible material or any other material that is formable and which is rolled before it is implanted by insertion into the kerf or which is implanted by pressing, pouring, squeezing or injecting the material into the kerf and the material then takes its shape as a strip following implantation.

The outer width of the cross-section of a strip is sometimes referred to herein as the outer width of the channel. References to such strip shapes herein each refer to the shape of a cross-section taken transverse to the length of the strip. In other embodiments one or more tubular elements are used to make the strip and these are disposed between the skull flap and the skull when the strip is implanted in a patient.

The surgical strips have side portions which are disposed between the skull flap and the skull when the strip is implanted. These side portions can optionally have openings such as holes, slits or lateral slots which permit bone regrowth. Additionally the slits may be oriented along a transverse axis through one sidewall and a portion of the bottom section of the strip, allowing the strip additional flexibility. The strips also can have a bottom portion. The tubular and solid shaped elements have bottom and top portions and these bottom and/or top portions also can have openings such as holes or lateral slots.

As a further option the cavities or tubular elements can be filled or partially filled with medication, bone paste, bone growth enhancers and the like. The putty-like, paste-like, gel-like or compressible material referred to herein also can be comprised of or impregnated with medication, bone paste, bone growth enhancers and the like.

Other variations and embodiments are described in more detail below and in the drawings and further variations will be apparent to those skilled in the art based upon the principles of the invention set forth herein.

BRIEF DESCRIPTION OF THE DRAWINGS

The appended drawings are not intended to illustrate every embodiment of the invention but they are representative of embodiments within the principles of the invention. The drawings are for illustrative purposes and are not drawn to scale.

In FIG. 21C the tubular strip has a helical slit along its length.

DESCRIPTION OF THE PREFERRED EMBODIMENTS

Figure 1:
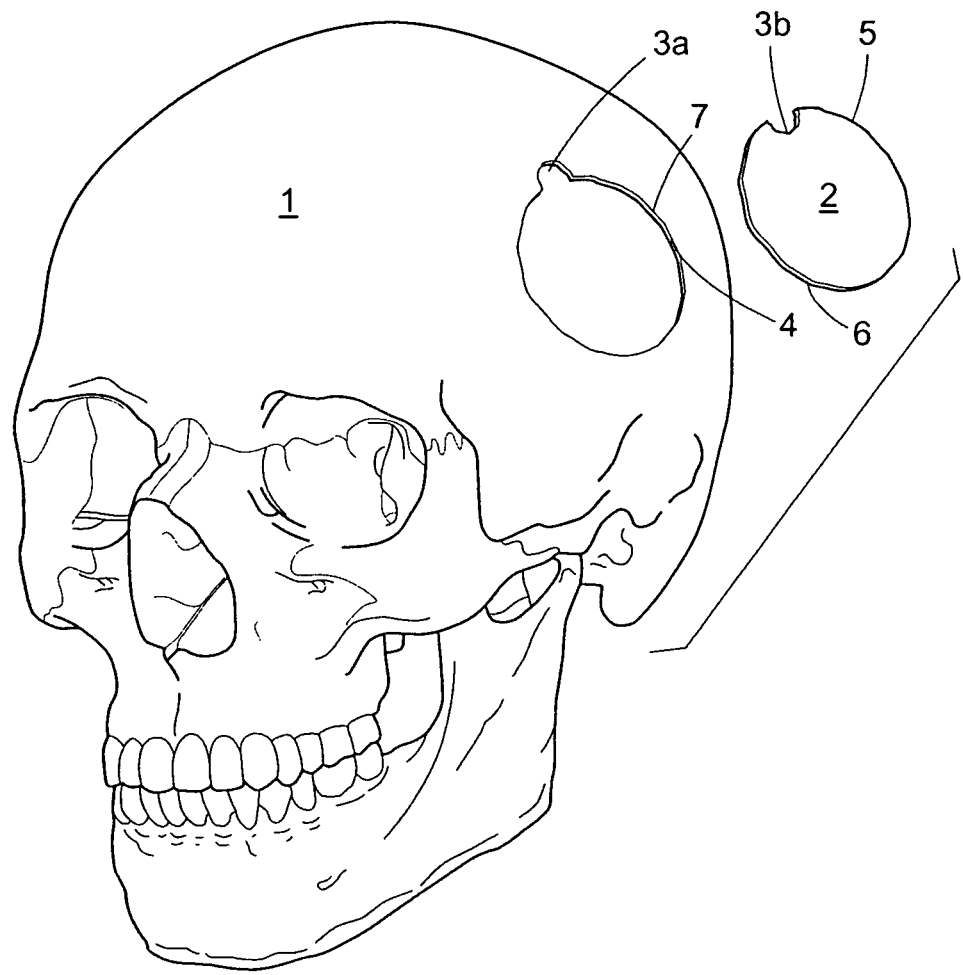
FIG. 1 is a representative view of a human skull showing one possible location and configuration of a craniotomy skull flap.

For reference, a human skull 1 with a craniotomy skull flap 2 (also referred to herein as a flap) is shown in FIG. 1. The skull flap 2 is defined by a burr hole 3 and the connecting osteotomy cut or kerf 4, wherein the skull portion of the burr hole is designated in FIG. 1 as 3a and the skull flap as 3b. The skull flap 2 has a perimeter contour 5 but it need not be of the particular shape shown and may have any number of burr holes 3. On the opposing sides of the osteotomy cut 4 is the respective bone edge surface 6 of the skull flap 2 and the surrounding bone 7 of the skull 1, respectively. The bone edge surface 6 has a perimeter contour 5 matching the contour of the surrounding bone 7 of skull 1.

Figure 1A:
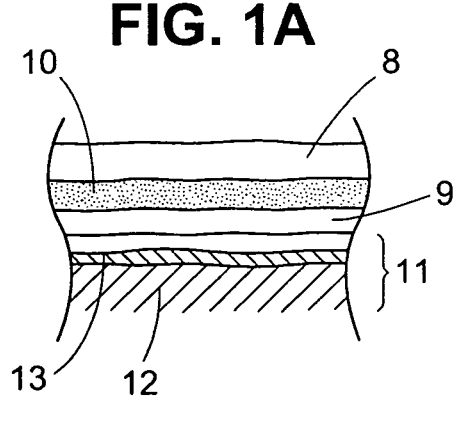
FIGS. 1A and 1B are section views of portions of skull bone and cranial cavity.
Figure 1B:
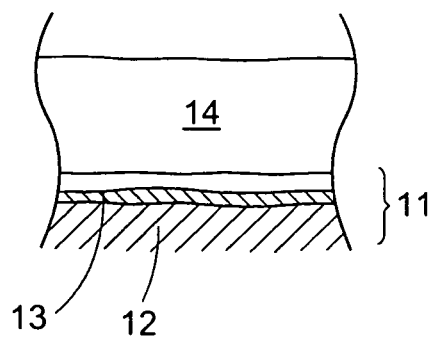

The skull 1 and skull flap 2 are either made from bone that has a three layer composition, as shown in FIG. 1A, or a single layer as shown in FIG. 1B. Referring to FIG. 1A, the outermost layer is the outer cortical bone 8 and the innermost layer is the inner cortical bone 9. Between these two stiff layers is a relatively soft middle layer of cancellous bone known as the diploe 10. Interior to the inner cortical bone 9 is the cranial cavity 11 housing the brain 12 and its surrounding dura matter 13. FIG. 1B illustrates the condition wherein the skull bone is comprised entirely of cortical bone 14.

The present invention is particularly adapted for securing a craniotomy skull flap 2 to the skull 1, but may be used in other situations where appropriate. The present illustrative discussion assumes that a surgical strip of the invention is being used in combination with a fastener of the invention to close a craniotomy skull flap 2 having one burr hole 3 but the same principles apply if the surgeon makes more than one burr hole in order to open up the skull for surgery. The kerf 4 may be normal to the surface of the skull 1 or at an angle thereto. As we shall explain in more detail below, angled cuts are presently preferred wherein the angle is such that the top of the skull flap 2 is larger relative the bottom than it would be if a cut normal to the surface of the skull was made. This is sometimes referred to herein as a "pumpkin cut" because the cut is similar to one made when cutting the top of a pumpkin to make a jack-o-lantern.

The term "surgical strip" is used herein to mean a surgical strip which is used in combination with a fastener of the invention.

The surgical strips of the invention, also referred to herein as strips, can be made straight or with a precurvature to reduce kinking when they are shaped to follow the perimeter contour of the skull flap.

The strips also can be made from a moldable material that has, for example, a putty-like, paste-like or gel-like consistency or a compressible material or any other material that is formable into a shape that will fit in the kerf. Strips of this type may be pressed, poured, squeezed or injected into a kerf and formed in situ. For example, a strip can comprise a paste-like or putty-like material containing bone, either allograft or autogenous bone, and/or other bone growth enhancing material.

Combinations of two or more than two strips of the invention can be used. Numerous variations are possible when such combinations are used as will be apparent to those skilled in the art based on the disclosures herein. For example, one strip may contain bone particulate and/or growth enhancers and another may contain antibiotics or other medications. Alternatively, one strip may be used as a floor for another strip. For example, a U, V, W or J-shaped strip or mesh or tubular strip may be threaded through or affixed to the projections of the fasteners to create a floor for a putty-like, paste-like, gel-like or compressible strip.

The fasteners and the surgical strips of the invention can be made of various biocompatible materials and combinations of biocompatible materials. Suitable materials include biocompatible metals, alloys, plastics and reinforced plastics which are commonly used in surgical implants of all kinds. Such materials include materials that have sufficient strength and flexibility to meet the objectives of the invention. The materials also can optionally be porous, semi-porous, semipermeable or maleable. Many of the materials that have been approved by the United States Food and Drug Administration (FDA) for surgical implant applications are also suitable. Some examples of suitable materials include DuraGen® dural graft matrix, available from Integra Lifesciences Corporation, 311 Enterprise Drive, Plainsboro, N.J. 08536, USA and Gelfoam® sterile compressed sponge, a product of Pfizer distributed by Pharmacia & Upjohn Company, Division of Pfizer Inc., New York, N.Y. 10017.

Generally speaking, there are three main types of alloys used in biocompatible metals today, titanium alloys, cobalt alloys and stainless steel alloys. An exhaustive list is available on the FDA website which also provides the reference numbers and effective dates of the ASTM or ISO standards for many of the materials that are suitable. Some examples include unalloyed titanium and titanium alloyed with aluminum, niobium and/or vanadium; stainless steel and other irons alloyed with molybdenum, chromium, cobalt, tungsten, aluminum, nickel, manganese or vanadium in various combinations, various other stainless steels and other iron alloys, for example, with aluminum oxides, zirconium oxides, tantalum and calcium phosphates. This list is not intended to be exhaustive.

Numerous types of high strength polymers also are employed to make implants and many of these are identified not only on the FDA website mentioned above but also on the ASTM website. Examples of suitable high strength polymers include polyetheretherketone (PEEK), epoxys, polyurethanes, polyesters, polyethylenes, vinyl chlorides, polysulfones, polytetrafluoro-ethylene (PTFE), polycarbonates, polyaryletherketone (PAEK), polyoxymethylene, nylon, carbon fiber polyester, polyetherketoneetherketoneketone (PEKEKK), silicones, hydrogels and the like. When a polymer is used, a small wire or other radiopaque material can be incorporated in the main body of the base for purposes of x-ray detection.

The foregoing lists of materials may have application in some embodiments of the present invention but not in others as will be apparent to those skilled in the art based on requirements of strength, flexibility, machinability and the like for the particular application. The lists are intended to be illustrative and not exhaustive. Other materials and new materials may be employed based upon the principles of the invention as set forth herein.

For purposes of this specification, the term "high strength polymer(s)" is defined as any biocompatible non-bioabsorbable polymer, copolymer, polymer mixture, plastic or polymer alloy having sufficient strength to withstand without failure the stresses that a fastener of the invention would normally be subjected to during surgery or in the body.

Bioabsorbable material can also be used to make all or a portion of one or more of the component parts of the fasteners or strips of the invention and/or the bioabsorbable material can be applied as a partial or complete coating on such component parts. Some component parts can be made from different materials than others as will be apparent to those having skill in the art based upon the disclosures herein.

The term "bioabsorbable material" as used herein includes materials which are partially or completely bioabsorbable in the body.

Suitable bioabsorbable materials include DuraGen, Gelfoam, collagen, polyglycolide, poly(lactic acid), copolymers of lactic acid and glycolic acid, poly-L-lactide, poly-L-lactate; crystalline plastics such as those disclosed in U.S. Pat. No. 6,632,503 which is incorporated herein by reference; bioabsorbable polymers, copolymers or polymer alloys that are self-reinforced and contain ceramic particles or reinforcement fibers such as those described in U.S. Pat. No. 6,406,498 which is incorporated herein by reference; bioresorbable polymers and blends thereof such as described in U.S. Pat. No. 6,583,232 which is incorporated herein by reference; copolymers of polyethylene glycol and polybutylene terephthalate, and the like. The foregoing list is not intended to be exhaustive. Other bioabsorbable materials can be used based upon the principles of the invention as set forth herein. Some of the most common:

| | |
|---|---|
| Poly-L-lactic acid (PLLA) | Poly-DL-lactic acid (PDLLA) |
| Polyglycolic acid (PGA) | Polydioxanone (PDS) |
| Polyorthoester (POE) | Poly-C-capralactone (PCL) |

Bioactive materials can be admixed with the bioabsorbable materials, impregnated in the bioabsorbable materials and/or coated on the outer surface thereof. Bioactive materials, including natural and/or synthetic materials, also can be used to fill cavities in the fasteners and the surgical strips. These materials can include, for example, bioactive ceramic particles, bone chips or paste, platelet rich plasma (PRP), polymer chips, synthetic bone cement, autologous materials, allograft, cadaveric materials, xenograft, nanoparticles, nanoemulsions and other materials employing nanotechnology, capsules or reinforcement fibers. And they can contain, for example, antimicrobial fatty acids and related coating materials such as those described in Published U.S. Patent Application No. 2004/0153125 A1; antibiotics and antibacterial compositions; immunostimulating agents; tissue or bone growth enhancers and other active ingredients and pharmaceutical materials known in the art.

The products of the invention which are made with bioabsorbable material can be made by molding, extrusion, heat shrinking or coating the bioabsorbable material on a base which has been provided with attachment means such as those described in our pending patent application Ser. No. 11/025,213 filed Dec. 29, 2004 which is incorporated herein by reference. Some of the screws and other fastening devices described in our pending patent application Ser. No. 11/025, 213 filed Dec. 29, 2004 can also be used in or in combination with the surgical strips and fasteners of the present invention. When the bioabsorbable material will have functional mechanical properties which are not made from the base material, the bioabsorbable material can be molded onto the base in the desired shape. Alternatively, the bioabsorbable material also can be coated, shrink wrapped or molded onto the base. If necessary, the bioabsorbable material can be machined to the desired shape and/or dimensions.

As will be apparent to those skilled in the art, the sizes of the surgical strips and fasteners of the invention can be varied to meet their intended applications. The shapes can take various forms in addition to those illustrated without deviating from the principles of the invention. And the sizes, lengths and widths can be varied for particular applications within the principles of the invention set forth herein.

Various methods can be used to employ the surgical strips and fasteners of the invention as will be apparent to those skilled in the art based upon the embodiment(s) of the surgical strips and fasteners selected for use by the practitioner. For example, the fastener may be attached to the skull flap first, then the skull flap would be positioned in the skull opening and the fastener would then be attached to the skull. In a preferred embodiment, the fasteners are made from a material that allows the flange to be intraoperatively bent so that the fastener and reattached flap will follow the original contour of the skull. The flange can be bent, for example, before it is affixed to the skull flap or after it is affixed to the skull flap, but normally it is automatically bent by the pressure imparted by the fasteners (screws, tacks, other means) when it is affixed to the skull. This could be followed by affixing one or more cranial plugs in the burr hole or holes as needed as described in our copending parent application Ser. No. 11/333,102 filed Jan. 17, 2006, the disclosure of which is incorporated herein by reference. In most embodiments, antibiotics, bone growth enhancers or other materials disclosed herein could be added in cavities in the surgical strips and/or fasteners before or after the skull flap is reattached to the skull, as will be apparent to those having ordinary skill in the art. It should be noted that the terms "affixing", "affixed" or "affix" as used herein include "snap-fit" and "press-fit" as well as the other means such as screws, staples, tacks, adhesives and the like as described herein. Other methods will be apparent to those having skill in the art depending upon the characteristics of the skull and/or skull flap, the type of surgery involved and the likelihood or unlikelihood of the need to re-open the surgical site.

As noted above, the surgical strips of the invention can be formed around the perimeter contour of the skull flap and attached to the skull flap or the strips can be attached to the fasteners before or after the fasteners are attached to the skull flap and before attachment of the flap to the skull. Alternatively, the fasteners can be attached to the skull flap and then the skull followed by insertion of a strip or strips. The step of attaching the fasteners to the skull flap, and optionally bending the flanges to conform with the skull contour, can be done by operating room personnel while the surgeon is performing surgery. This saves substantial time when the skull flap is reattached following surgery. The previously attached fasteners support the skull flap and insure that the top of the flap coincides with the top surface of the skull. As noted above, the shape of the skull flap is highly variable and when it is reattached to the skull it is positioned in a manner to match the position from which it was removed, similar to replacing a piece of a jigsaw puzzle.

There are numerous suitable options for fastening the fasteners of the invention to the skull flap and the skull. These include screws, staples, tacks, glues, adhesives, peel off adhesives, press-fit, snap-fit and combinations of two or more thereof. For example, a fastener may be stapled onto the skull flap and then press-fit into the opening in the skull. These fastening methods may be used to affix the fasteners to any contacting surface of either the skull flap or skull.

Figure 2:
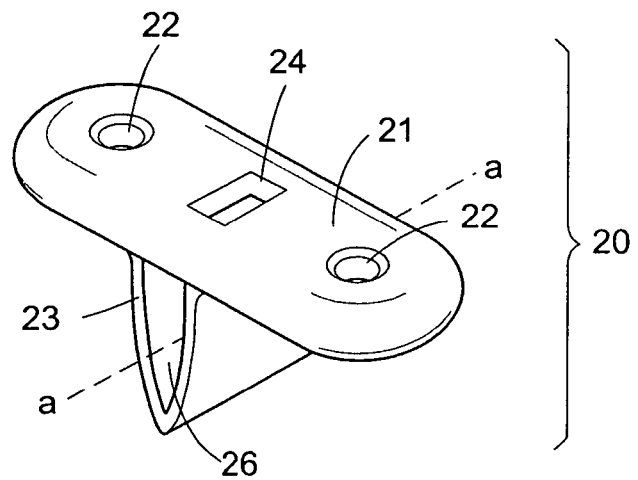
FIG. 2 is a perspective view of a fastener of the invention having a V-shaped projection extending from the bottom of a flange. The projection has an aperture therethrough.
Figure 2A:
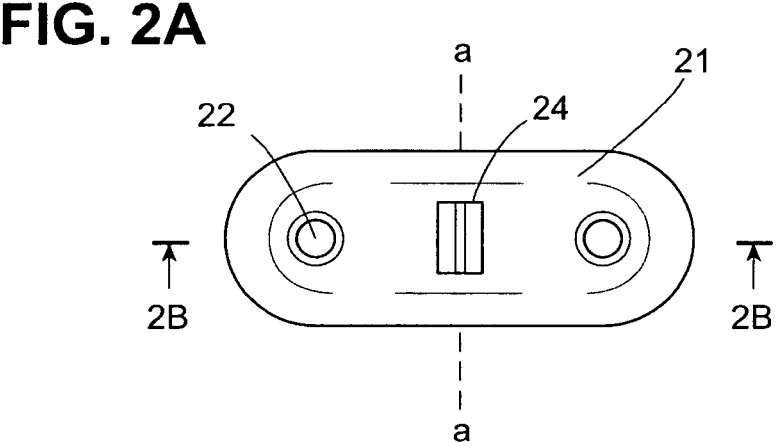
FIG. 2A is a top view of the fastener and FIG. 2B is a section view.
Figure 2B:
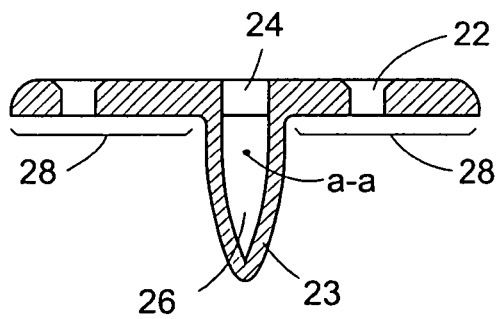

FIG. 2 is a perspective view of a fastener 20 of the invention. FIG. 2A is a top view and FIG. 2B is a section view. A continuous elongate flange 21 has lower surfaces 28 which overlay both sides of the kerf when the fastener is affixed to the skull and skull flap. Optional holes 22 can be provided for screws or other devices for affixing the fastener to the skull and skull flap. A V-shaped projection 23 extends from the underside of the flange. The projection 23 has an aperture 26 having a central axis a-a disposed in parallel with lower surfaces 28 and a surgical strip 27 can be threaded through the aperture as illustrated in FIG. 2D and the section view thereof, FIG. 2E. Optional opening 24 provides access to aperture 26 after fastener 20 is installed in a patient. The opening 24 opens from the upper surface of the flange 21 into the aperture 26 and can be used to assist in threading a strip or strips through the aperture and/or to insert medication, bone growth enhancers and the like into the fastener.

Figure 2C:
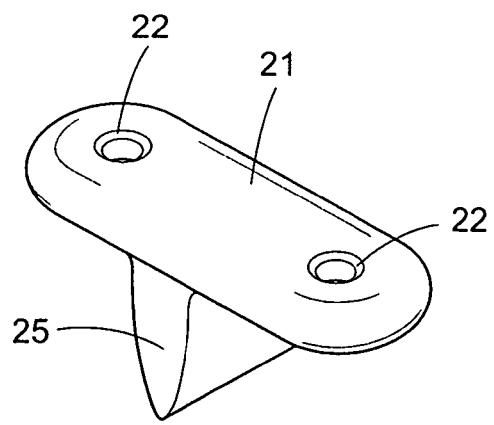
FIG. 2C illustrates a fastener with a solid V-shaped projection.
Figure 2D:
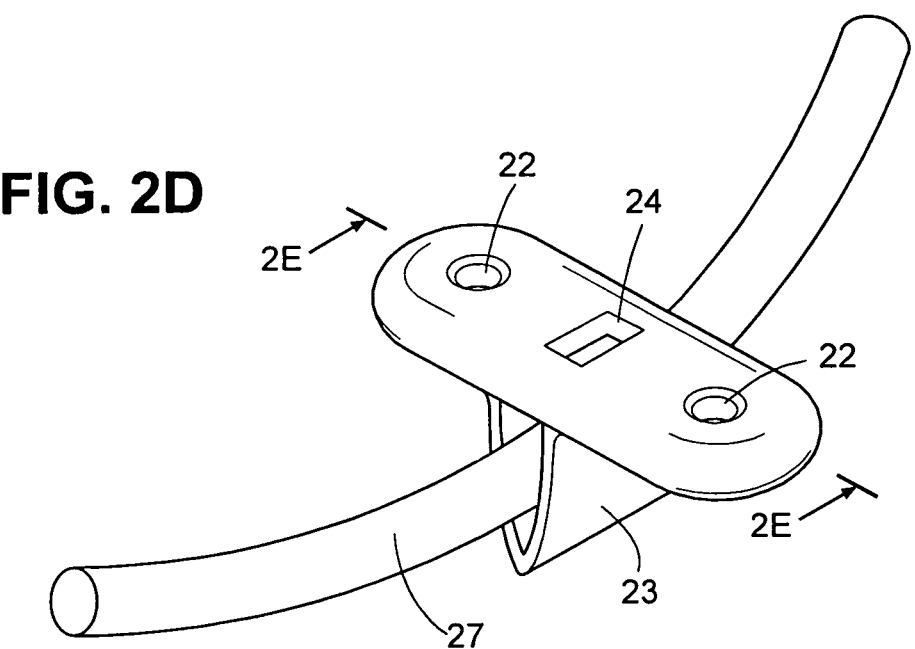
FIG. 2D is a perspective view of the FIG. 2 fastener having a strip threaded through the aperture thereof and FIG. 2E is a section view of FIG. 2D.
Figure 2E:
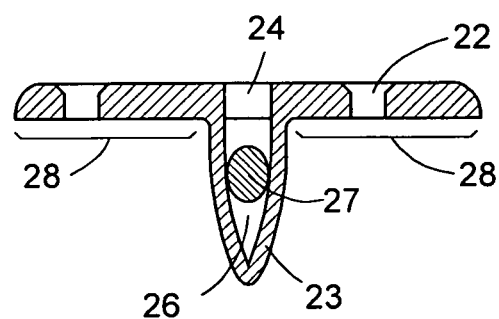
Figure 3:
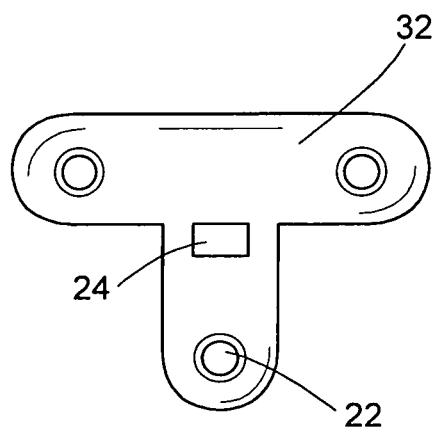
FIGS. 3, 3A, 3B and 3C are top views illustrating various shapes of the flange portion of the same type of fastener as illustrated in FIG. 2.
Figure 3A:
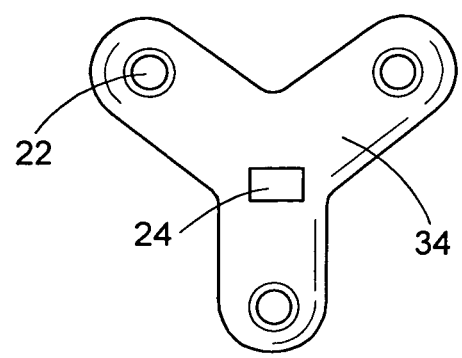
Figure 3B:
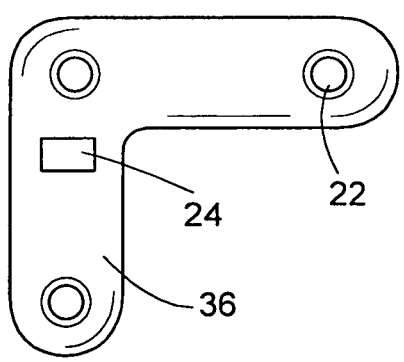
Figure 3C:
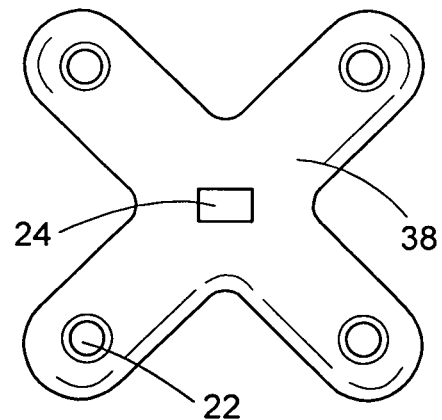

FIG. 2C illustrates an alternative embodiment of the fastener wherein the projection 25 is solid and does not have an aperture or an optional opening through the flange.

FIGS. 3, 3A, 3B and 3C are top views of fasteners of the invention having flanges of various shapes. Flange 32 is T-shaped, flange 34 is Y-shaped, flange 36 is L-shaped and flange 38 is X-shaped. Other shapes can be used without departing from the invention.

Figure 4:
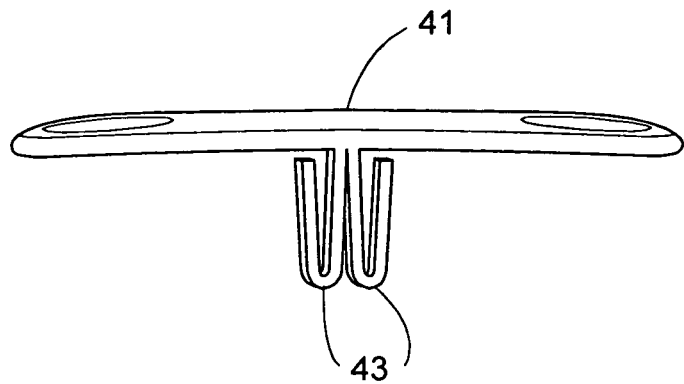
FIG. 4 is a perspective view of a fastener of the invention having a "W" shaped projection extending from the bottom of the flange.
Figure 5:
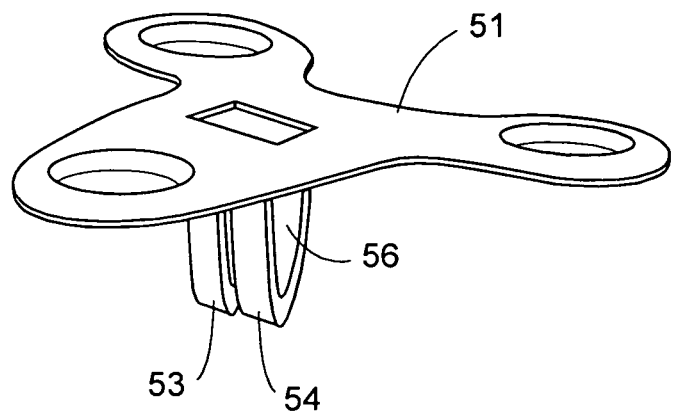
FIG. 5 is a perspective view of a fastener of the invention having a Y-shaped flange and two V-shaped projections.
Figure 6:
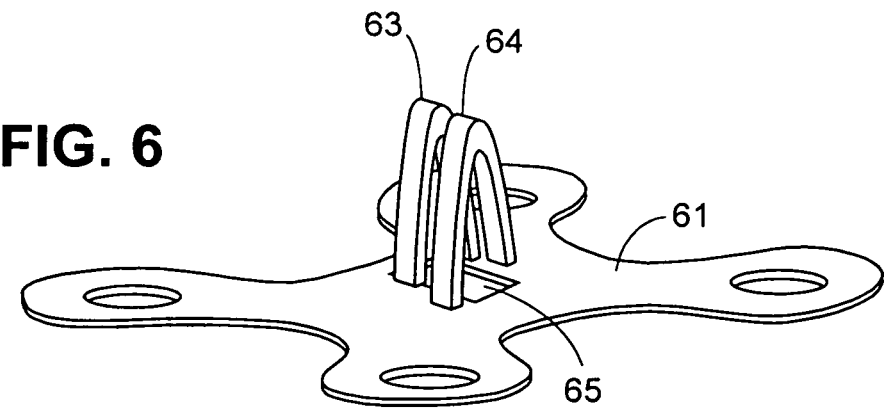
FIG. 6 is a perspective view of the underside of a fastener of the invention having an X-shaped flange and two V-shaped projections wherein each projection is connected on one side and the connections are on opposite sides of an opening in the flange.
Figure 7:
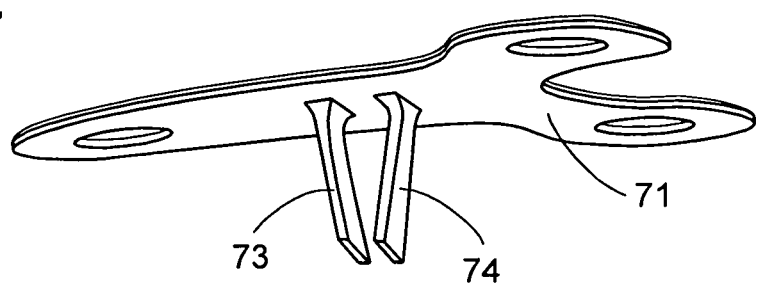
FIG. 7 is a perspective view of a fastener of the invention having a Y-shaped flange and two projections from the underside.
Figure 8:
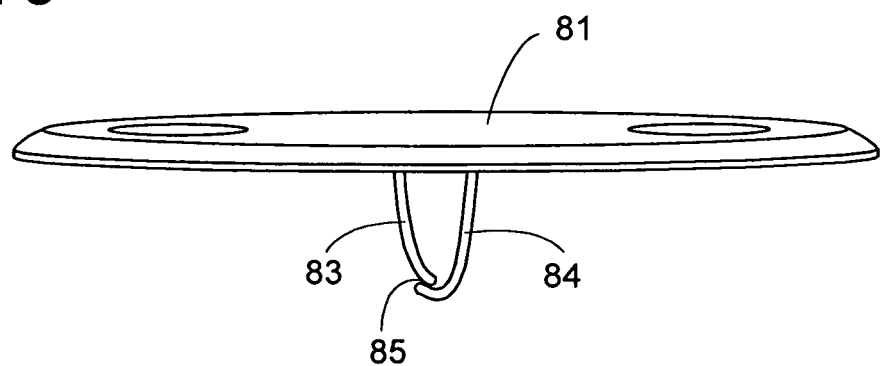
FIG. 8 is a perspective view of a fastener of the invention having a severed V-shaped projection.
Figure 9:
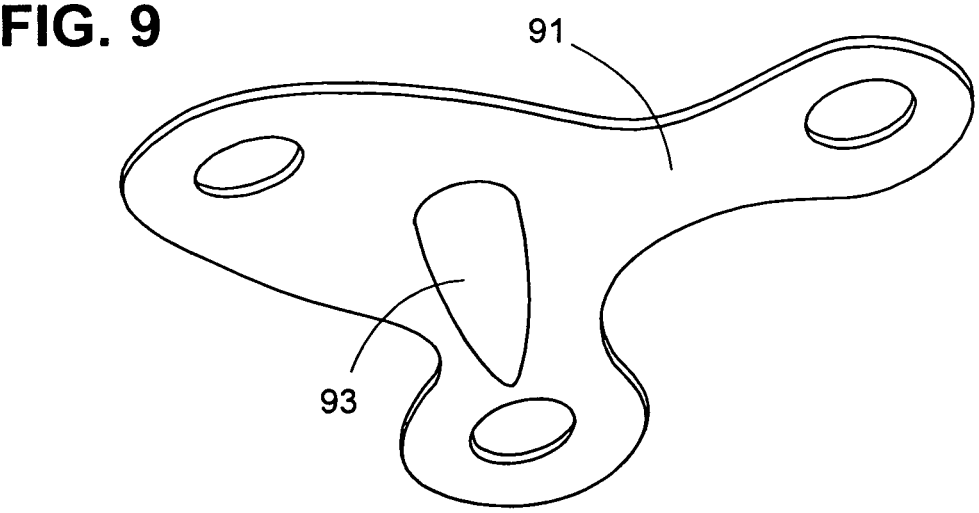
FIG. 9 is a perspective view of a fastener of the invention having a modified conical projection.

The projections from the undersides of the flanges can also have various shapes without departing from the invention and there can be one or more than one projection from the underside of a flange. FIG. 4 illustrates a fastener having projections 43 which make up a W-shape extending from elongate flange 41. FIG. 5 illustrates a fastener having Y-shaped flange 51 having V-shaped projections 53 and 54 extending from the underside thereof. Apertures 56 in the projections are coaxial. An X-shaped flange 61 is provided in the fastener of FIG. 6. One leg of projection 63 is connected to the underside of the flange on one side of opening 65 and one leg of projection 64 is connected to the underside of the flange on the opposite side of opening 65. The unconnected legs of the projections allow for enhanced flexibility. The fastener illustrated in FIG. 7 is comprised of a Y-shaped flange 71 and projections 73 and 74. Flange 81 of the fastener illustrated in FIG. 8 has projections 83 and 84 which together form the shape of a V which has been severed at point 85. A modified conical or bullet-shaped projection 93 extends from the bottom of flange 91 in the fastener of FIG. 9. Projection 93 can be solid or hollow.

In the prior art, flat plates were typically used to reattach a skull flap to a skull. The plates did not have projections as described herein. By sizing the projection so that its width corresponds to the diameter of the cutting burr of a craniotome cutter, and consequentially the width of the kerf around the skull flap, the projection centers the flap and allows the surgeon to place the flap in the position it occupied before it was cut out of the skull. The projection also acts as a buttress to resist inward displacement of the flap and can serve to intraoperatively bend the flange of the fastener or assist the manual bending of the flange to match the contour of the skull. Because the skull flap is cut out in a single pass with the craniotome, the resulting gap (the kerf) between the native skull and flap necessarily corresponds to the width (diameter) of the cutting burr. To replace the flap in its original position, the surgeon needs to maintain this uniform gap around the periphery of the flap as he/she applies the rigid fixation using the fasteners. By matching the width of the projection on the fastener to the diameter of the cutter, this is automatically accomplished.

Figure 10:
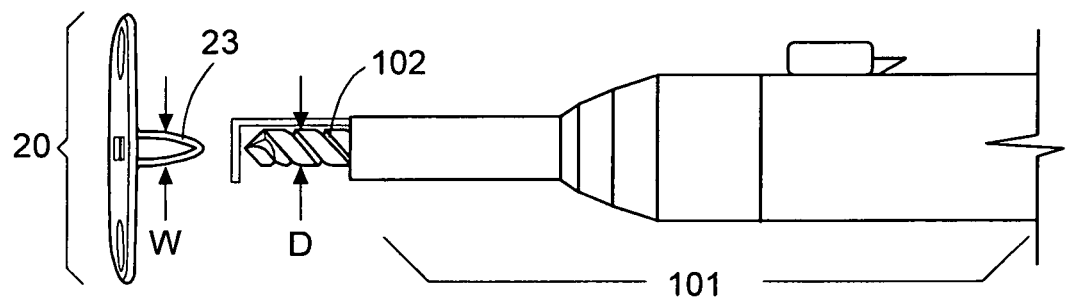
FIG. 10 illustrates a craniotome having a cutting diameter of generally the same width as the projection of a fastener.

FIG. 10 illustrates a craniotome 101 with a footplate 103 and a cutting burr 102 having relatively the same diameter D as the width W of projection 23 from fastener 20.

Figure 11:
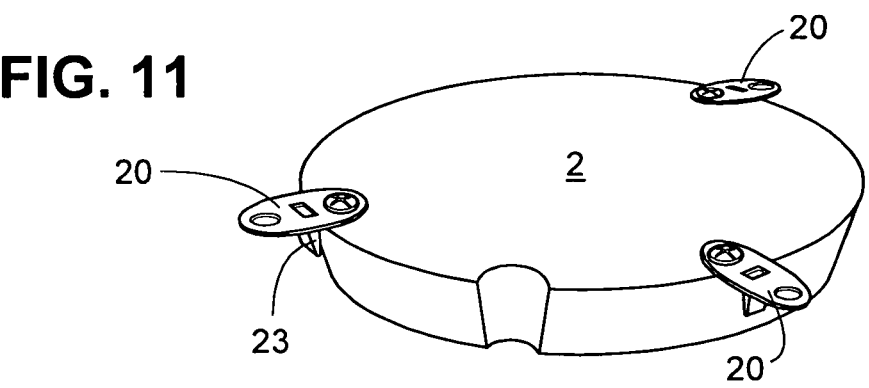
FIG. 11 is a perspective view of a skull flap having three fasteners positioned thereon for affixation thereto.

In a preferred surgical method, the fasteners 20 are affixed to the skull flap 2 before the skull flap is reattached to the skull. This is illustrated in FIG. 11 wherein one side of each projection 23 is butted up against and in contact with the perimeter of the flap, the side being approximately tangential to the edge of the flap at the point of contact. The number of fasteners employed is at the discretion of the surgeon. We recommend using at least two and preferably three fasteners or more to insure proper placement of the flap into its original position.

Figure 12:
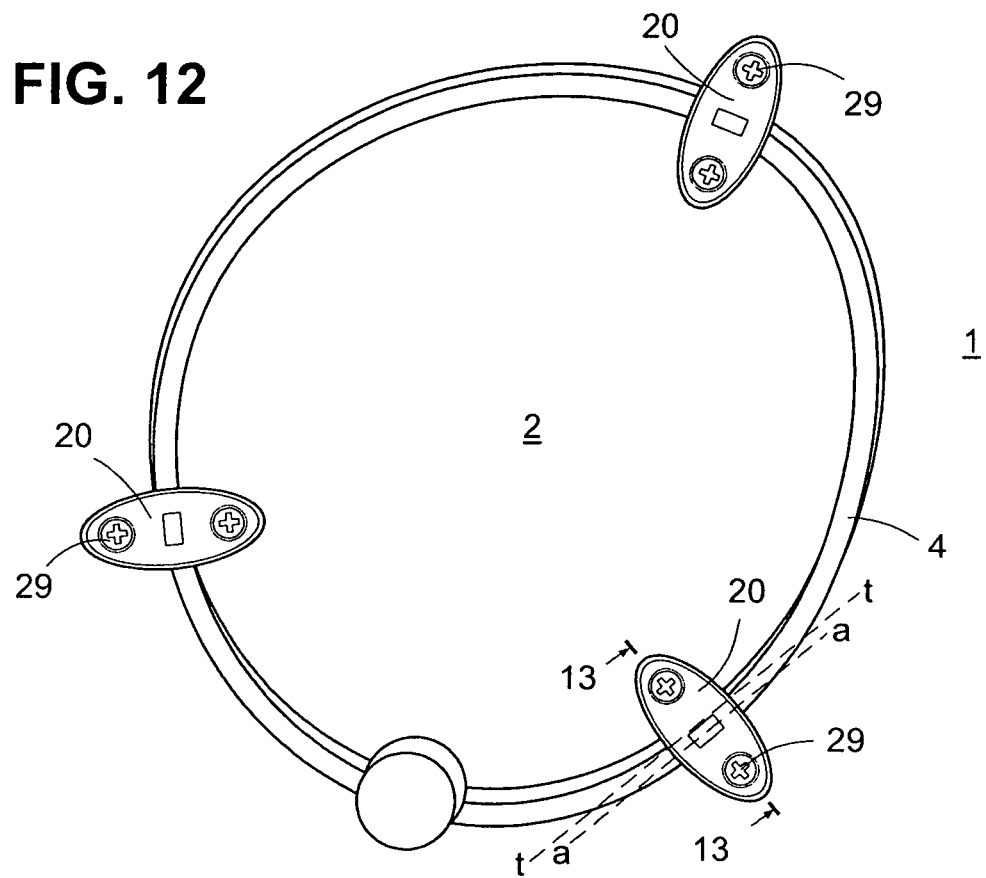
FIG. 12 illustrates a skull flap reattached to a skull using the fasteners of the invention which have been installed with screws.

When the flap 2 is replaced in the skull 1, the fasteners 20 insure an even gap (i.e., the kerf 4) around the periphery thereby returning the flap to its original position as illustrated in FIG. 12. Screws 29 are used to affix the fasteners 20 to the skull flap and skull in the illustration but it is understood that other devices or adhesives can be used to affix the fastener as previously described herein.

Figure 13:
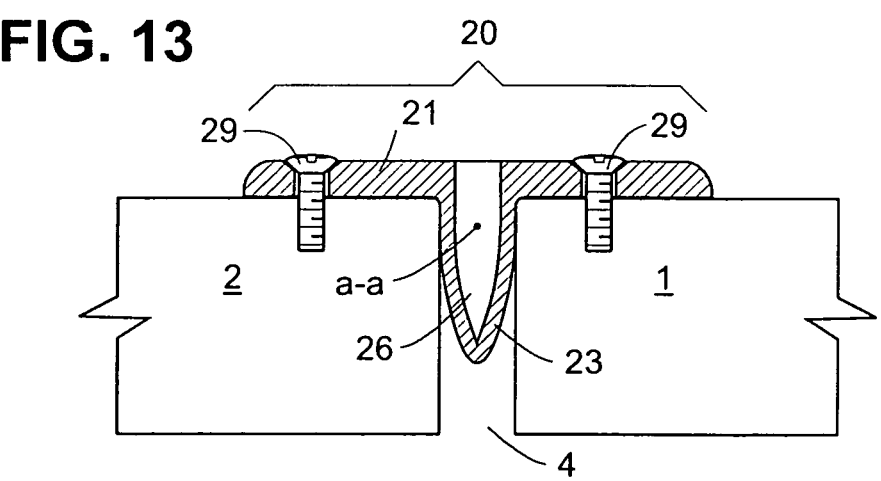
FIG. 13 is a section view of a skull flap reattached to a skull including a section of a fastener of the invention.

FIG. 13 is a section view of a portion of FIG. 12 illustrating the relationship of the fastener 20 to the skull flap 2 and skull 1 after the skull flap has been reattached to the skull. The projection 23 fits snugly between the sidewalls of the kerf 4 and the central axis a-a of aperture 26 is approximately in parallel with the side walls at the points of contact of the projection with the sidewalls. Stated another way, the central axis a-a of the aperture is approximately in parallel with the perimeter (or a tangent t-t to the perimeter) at the point of contact of the projection with the surface of the perimeter.

Restoration of the original flap position provides the optimum cosmetic result and the consistent peripheral gap (the kerf) allows for the insertion of a uniform volume of material all around the flap. This inserted material comprises one or more strips of the invention. For example, the material could be autologous bone graft as described above, autogenous bone mixed with blood and/or saline, a filler material such as collagen, DuraGen, Gelfoam or the like, or a combination of bone graft material and filler. These materials act as strips whether or not they are supported by the fasteners.

Figure 14:
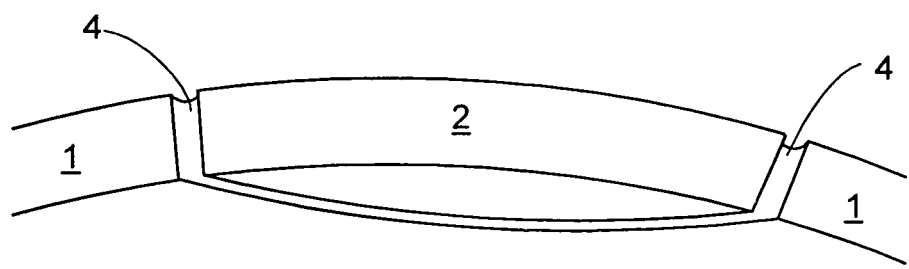
FIG. 14 illustrates in section a conventional craniotome cut to remove a skull flap from a skull.
Figure 14A:
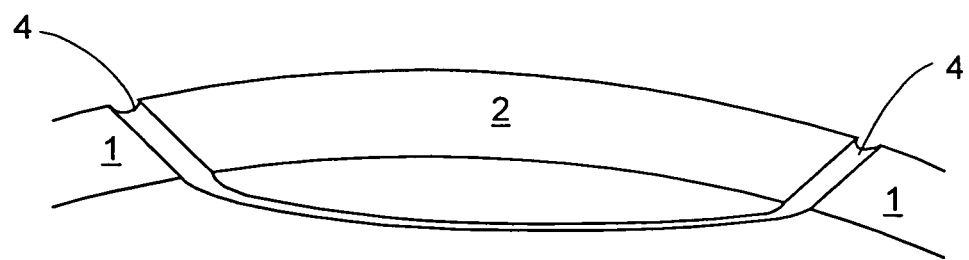
FIG. 14A illustrates in section a more angled cut (sometimes referred to herein as a "pumpkin cut") to remove a skull flap from a skull.

When cutting the flap, the surgeon will keep the craniotome angled perpendicular (normal) to the curvature of the skull or more likely, he/she will deliberately tilt the cutter to produce an angled cut through the skull to make a pumpkin cut as described above. This is illustrated in FIGS. 14 and 14A wherein the cut in FIG. 14 is normal to the skull and the cut in FIG. 14A is a pumpkin cut.

Both methods produce a flap that is widest at its outer or top surface and tapers to a smaller dimension across its inner or bottom surface. The corresponding sidewalls of the kerf 4 are generally in parallel. While neither flap would fall freely through the corresponding hole in the skull, allowing the bone flap to move or settle inwardly would cause the inner surface of the flap to impinge on the brain and would secondarily result in a cosmetically unacceptable depression of the patient's scalp. Rigid fixation of the flap to the skull solves this problem. Prior art metallic plates without a projection span the gap between flap and skull and are generally affixed with screws anchored into the bone. But the projection beneath the flange of the fastener of the invention adds an additional element of strength. It does so without adding any additional material to the surface of the skull which would increase the chance that the fixation system of the invention would be palpable to the patient.

The fastener has a top flange that functions much like a standard bone plate but the addition of the projection beneath the flange fills the gap created by the osteotomy cut (kerf) and acts as a buttress to further resist any downward force on the flap. Because the width of this projection is matched to the craniotome cutting burr, the lateral walls of the projection are either in contact with or in very close proximity to the parallel sidewalls of the flap and skull as shown in FIG. 13. Any inwardly directed force on the flap must now overcome not only the resistance of the flange (in bending) and screws or other anchoring devices but also must crush the projection which fills the gap.

Because the width (or diameter) of the projection on the fastener matches the diameter of the craniotome cutting burr, the projection effectively restores the removed bone volume at each fastener location. This allows it to function as a three-dimensional spacer, automatically restoring the flap location side-to-side as well as re-establishing the correct depth of the flap relative to the skull as shown here.

There is one other advantage attributable to the underside projection on the fastener. The difficulty of bending plastic plates (without heating and softening) can be overcome with the fastener design. When the flap with attached fastener is reinserted into the skull opening, the projection will be pushed slightly toward the side of the flap. This in turn will bend the flange of the fastener slightly downwardly. Because the projection is trapped in the gap between the flap and the skull, this bend is maintained. The surgeon simply pushes the flap down (inward) and the non-secured end of the flange bends to meet the skull. The surgeon then fastens this side in place with the appropriate affixation device or adhesive. This feature allows a fastener to be made with a flange that is only slightly precurved knowing that it will self-bend when the flap is inserted into the skull opening. Because the projection provides added support, this flange can be made more flexible than a traditional plate to enhance this property.

Figure 15:
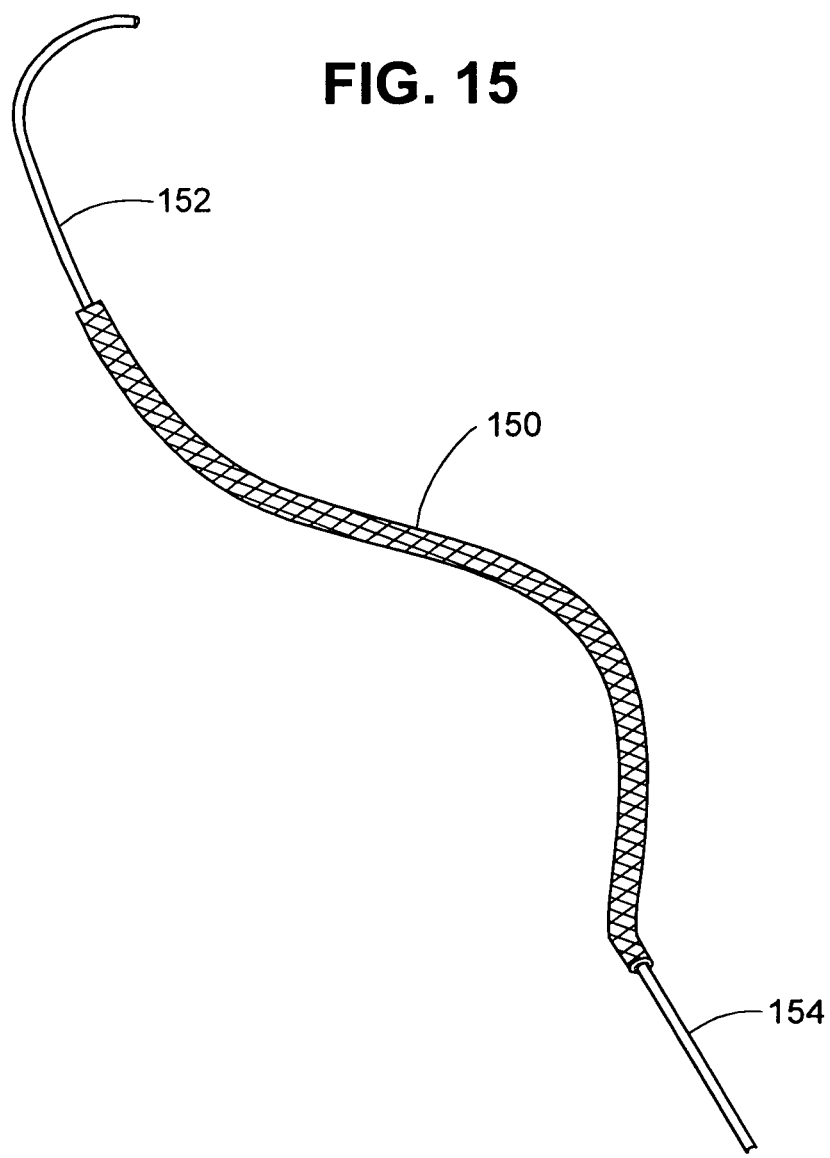
FIG. 15 is a perspective view of a woven strip with leaders to thread the strip through apertures in the projections of the fasteners of the invention.

FIG. 15 illustrates a mesh strip 150 having a curved leader 152 affixed to one end thereof. An optional leader 154 affixed to the other end is also illustrated. The leader or leaders can be pre-curved, straight or intraoperatively curved. This embodiment can be used when the strip is to be threaded through the apertures 26 in the fasteners. The leader is used in a similar manner to a needle when sewing with a needle and thread. Any of the strips of the invention that are sufficiently flexible can be combined with a leader in this manner.

Figure 16:
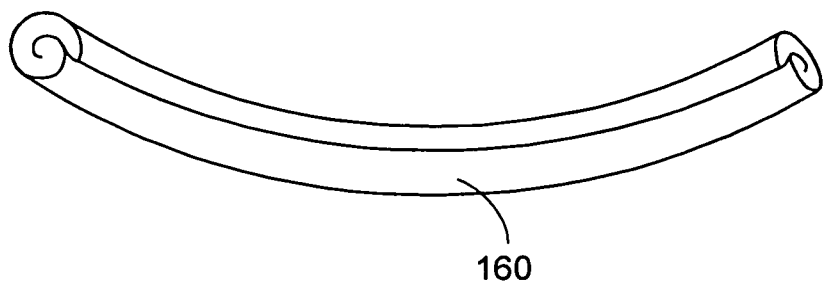
FIG. 16 illustrates a rolled strip of a putty-like, paste-like, gel-like or compressible material which can be used as a strip of the invention.

FIG. 16 illustrates a strip 160 made from a putty-like or gel-like material. This can be made in the form of a rolled material as illustrated or it can be hand rolled or compressed and pressed into the kerf after the skull flap is reattached to the skull (illustrated as strip 161 in FIGS. 17A and 17B). Alternatively, this type of filler material can simply be pressed, poured or injected into the kerf after reattachment of the flap, effectively creating a strip of material in situ in the kerf extending from one fastener to another. As noted above, the objectives of all of the strips of the invention are to close the openings in the skull and optionally to enhance bone regrowth, provide medication and the like.

The strips also can serve to provide a "floor" to the kerf. This prevents filler strips (implanted following implantation of the strip or strips which provide a floor) such as autologous bone which are pressed into the kerf, from migrating into the cranium. Furthermore, the strips which serve to provide a floor replace some of the volume of the bone removed with the craniotome so that collected bone from the craniotome will be adequate to fill the volume remaining in the kerf.

The strips of the invention can be made from various materials and in various shapes. They can be affixed to the skull flap before it is reattached to the skull, they can be affixed to the fasteners before or after they are affixed to the skull or they can be implanted after reattachment. Some of them can be threaded through apertures in the fasteners, others can be affixed to or implanted adjacent to the sidewall of the skull flap and others can simply be inserted adjacent the fasteners and in attachment with or in contact with the fasteners or without necessarily being attached to or in contact with the fasteners.

Figure 17:
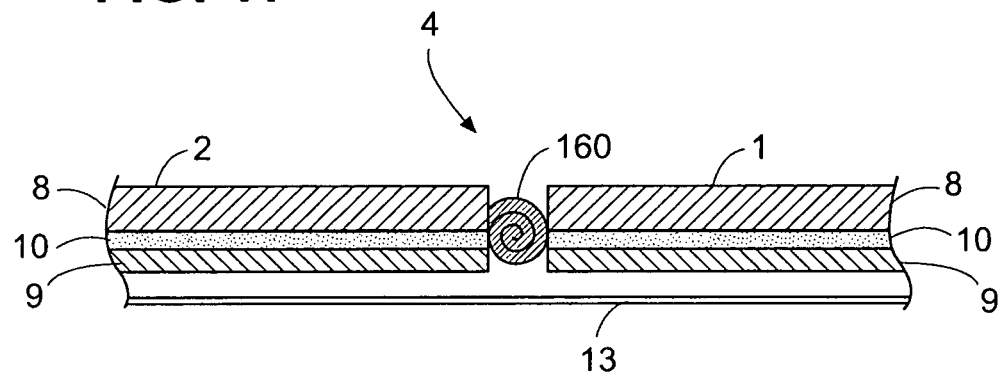
FIG. 17 is a section view illustrating the relationship of the strip of FIG. 16 to the skull flap and the skull.
Figure 17A:
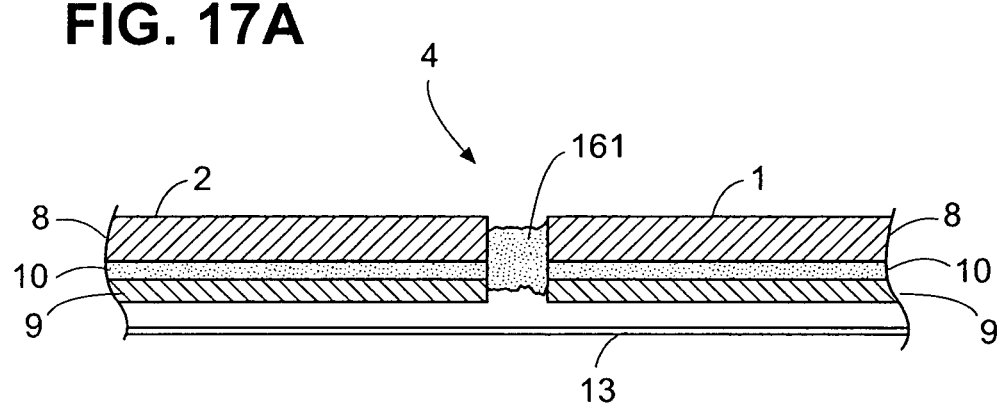
FIG. 17A is a section view illustrating the relationship to the skull flap and the skull of a strip 161 which has been pressed into the kerf and formed in situ.
Figure 17B:
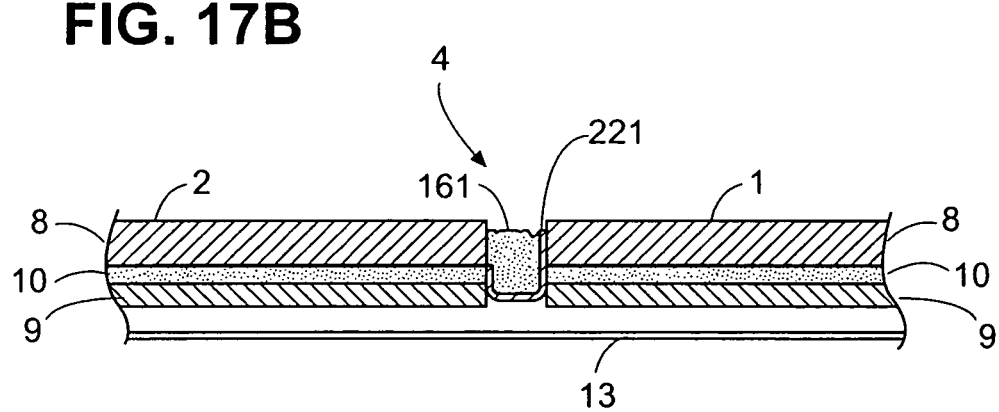
FIG. 17B illustrates the use of a U-shaped strip as a "floor" for strip 161.

FIG. 17 is a section view of strip 160 implanted between a skull flap 2 and a skull 1. In FIGS. 17A and 17B the strip 161 is comprised of a putty-like, paste-like, gel-like or compressible material which is pressed into the kerf 4 to form a strip in situ. FIG. 17B illustrates an embodiment employing a U-shaped strip 170 which is used as a "floor" for the strip 161 so that the material of strip 161 (or any other material or strip in the place of strip 161) will not impinge upon the dura or migrate into the cranium. Of course various other strips of the invention can be used as a floor or as a filler to provide medication, enhanced bone regrowth, etc. as will be apparent to those having skill in the art based on the disclosures herein.

Figure 18:
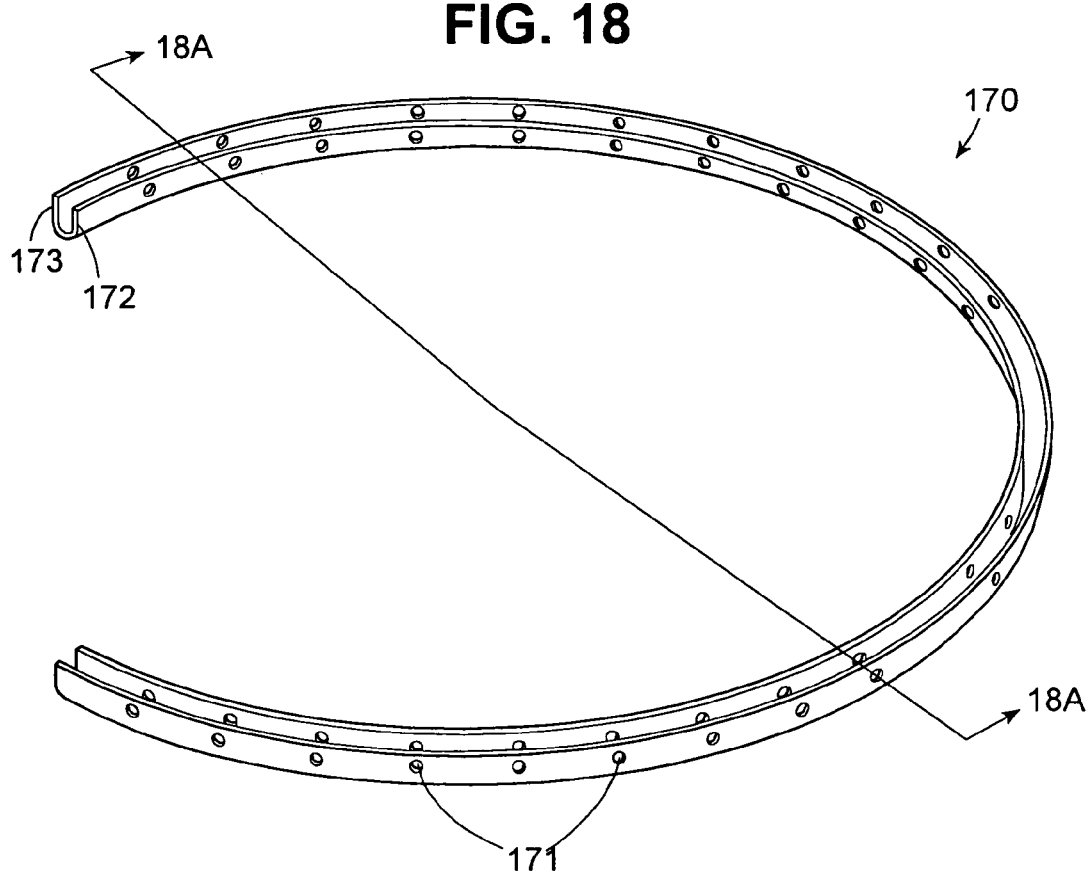
FIG. 18 is a perspective view of an embodiment of a strip of the invention comprising a perforated, U-shaped, flexible strip
Figure 18A:
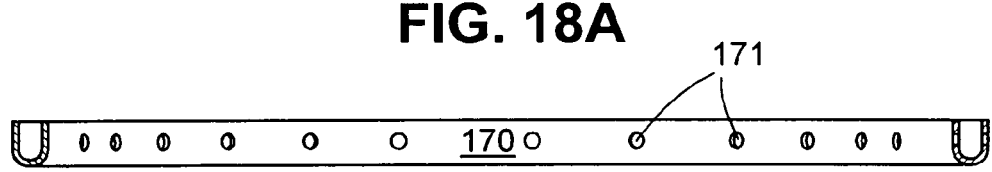
FIG. 18A is a section view of the FIG. 18 embodiment.

FIGS. 18 and 18A illustrate a strip 170 having a U-shape which is pre-curved and sufficiently flexible to be shaped to follow the perimeter contour of a skull flap. Multiple holes 171 are disposed around the inside perimeter 172 and the outside perimeter 173 of U-shaped strip 170. The holes 171 permit bone growth for bone to bone reattachment of the skull to the skull flap or they can be used to affix the sidewalls of the strip to the edges of the skull flap. Bone growth can be enhanced by filling the U-shaped strip 170 with known bone growth enhancers and/or other bioactive materials as described above. This can be done before and/or after the strip 170 is implanted in the patient. This concept can be adapted by those skilled in the art to strips of other cross sections disclosed herein.

Figure 19:
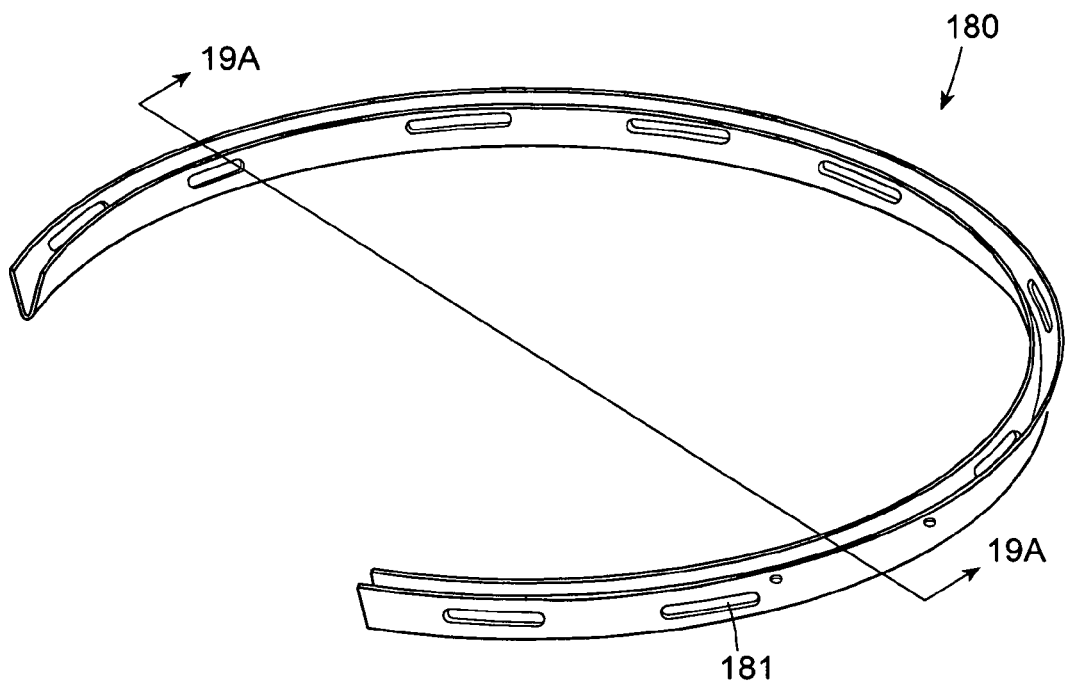
FIG. 19 is a perspective view of an embodiment of a strip of the invention comprising a V-shaped flexible strip and FIG. 19A is a section view of the FIG. 19 embodiment.
Figure 19A:
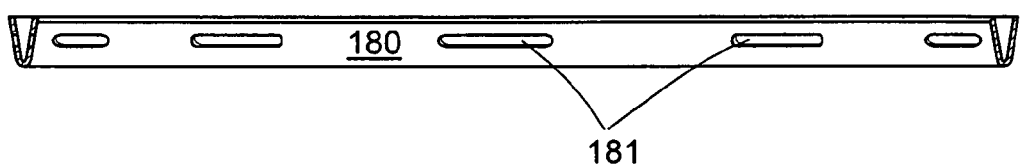
Figure 19B:
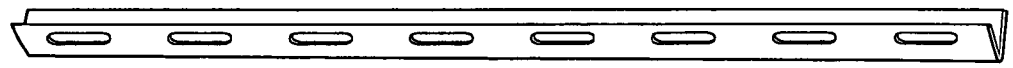
FIG. 19B is a perspective view of the FIG. 19 embodiment which is straight rather than pre-curved.

FIGS. 19 and 19A illustrate a strip 180 comprised of a V-shaped strip which is pre-curved and sufficiently flexible to be shaped to follow the perimeter contour of a skull flap. Multiple slots serve the same function as the holes 171 described in respect of the FIG. 18 embodiment and the V-shaped strip 180 can be filled with known bone growth enhancers and/or other bioactive materials and/or medications as described above. FIG. 19B is a perspective view of the FIG. 19 embodiment which has not been pre-curved.

Figure 20:
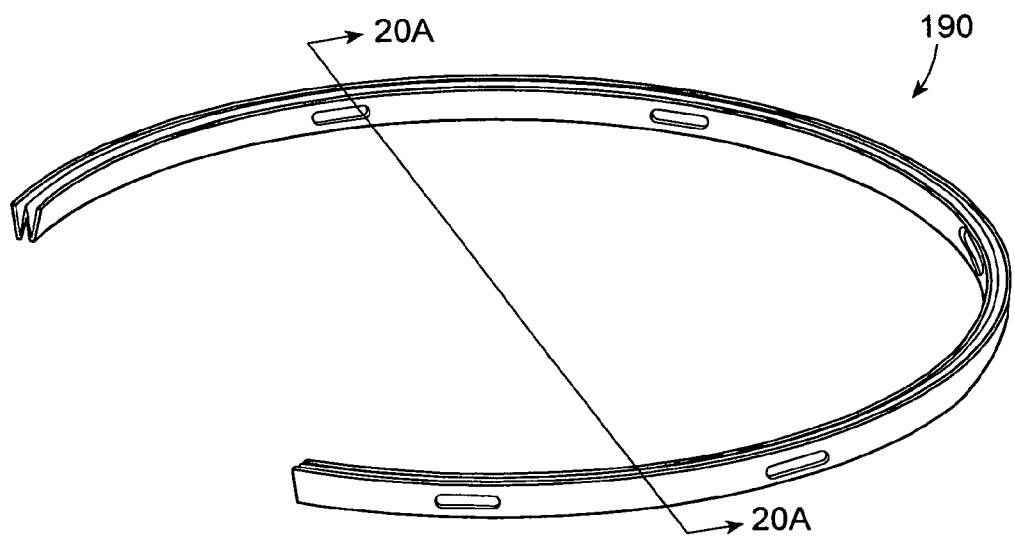
FIG. 20 is a perspective view of an embodiment of a strip of the invention comprising a W-shaped flexible strip and FIG. 20A is a section view of the FIG. 20 embodiment.
Figure 20A:
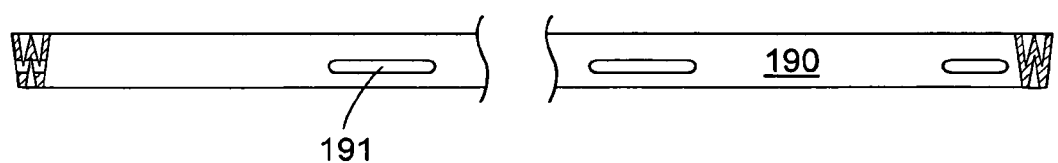

The strip 190 illustrated in FIG. 20 is comprised of a W-shaped strip which is pre-curved and sufficiently flexible to be shaped to follow the perimeter contour of a skull flap. Slots 191 or holes (not shown) can optionally be provided through the W-shaped strip to serve the same functions as described above.

Figure 21:
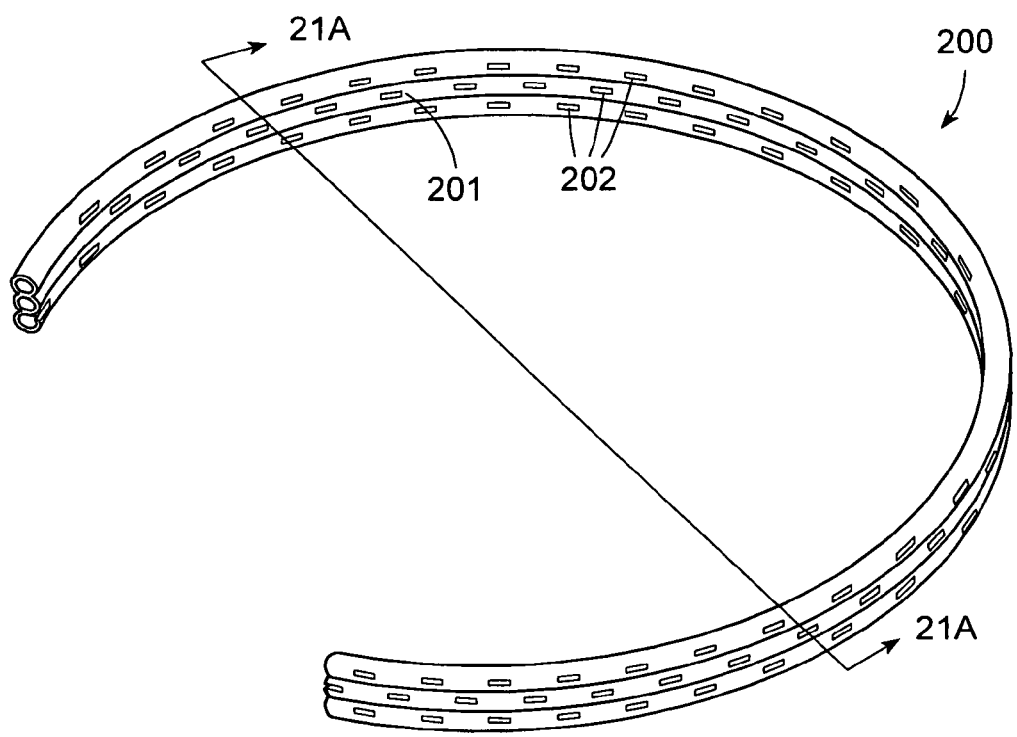
FIG. 21 is a perspective view of a strip of the invention having a flexible strip comprised of three stacked tubes and FIG. 21A is a section view of the FIG. 21 embodiment.
Figure 21A:
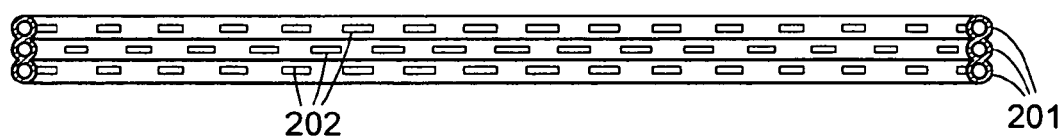

Strip 200 illustrated in FIG. 21 is comprised of one or more flexible tubes 201 (three illustrated) which are pre-curved and sufficiently flexible to be shaped to follow the perimeter contour of a skull flap. The terms "tubular" or "tube" as they are used herein are not meant to restrict the lateral cross-section of the tube to only a circular profile. Oval, elliptical, rectangular or other closed geometric shaped tubular structures (not shown) are also within the meaning of "tubular" or "tube" and can be used with this design. A tube of the invention can be hollow, filled or solid. Multiple slits 202 or holes or slots (not shown) can optionally be provided in the tubes 201 as with many of the other embodiments discussed above. The slits 202 are narrow cuts made through the tubes 201. The tubes 201 also can be filled with known bone growth enhancers and/or other bioactive materials as described above. These tubular strips may be packaged (sterile) with the bioactive materials already filling the cavities. This is also possible for the other configurations but obviously much more practical for a tubular profile.

Figure 21B:
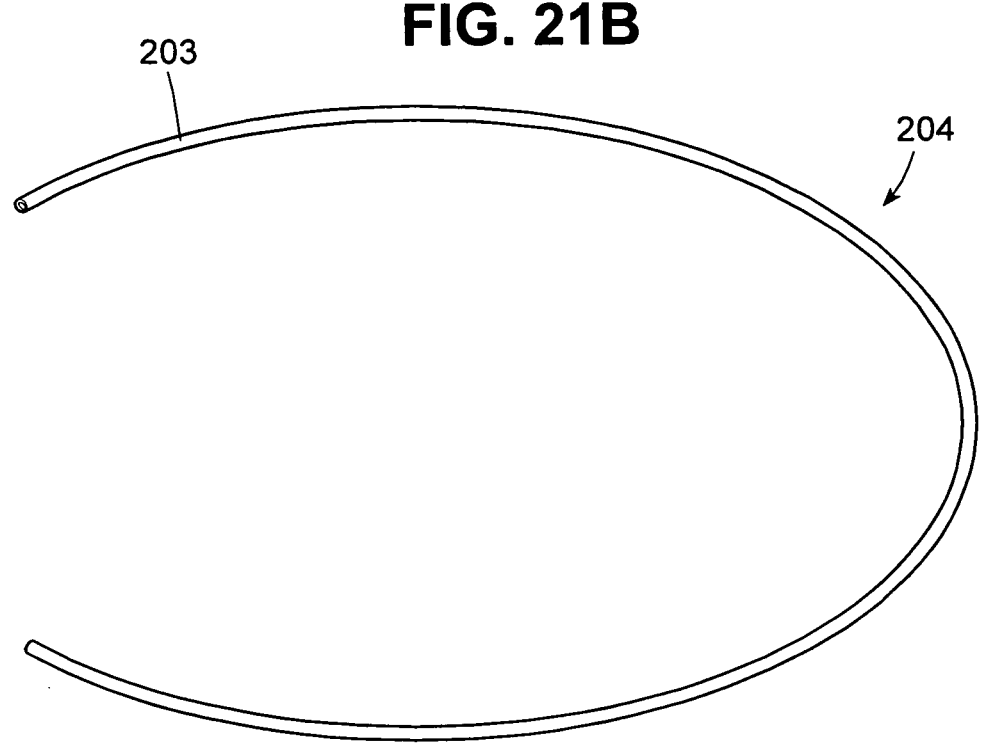
FIGS. 21B and 21C are perspective views of flexible tubular strips which also can be filled or solid.
Figure 21C:
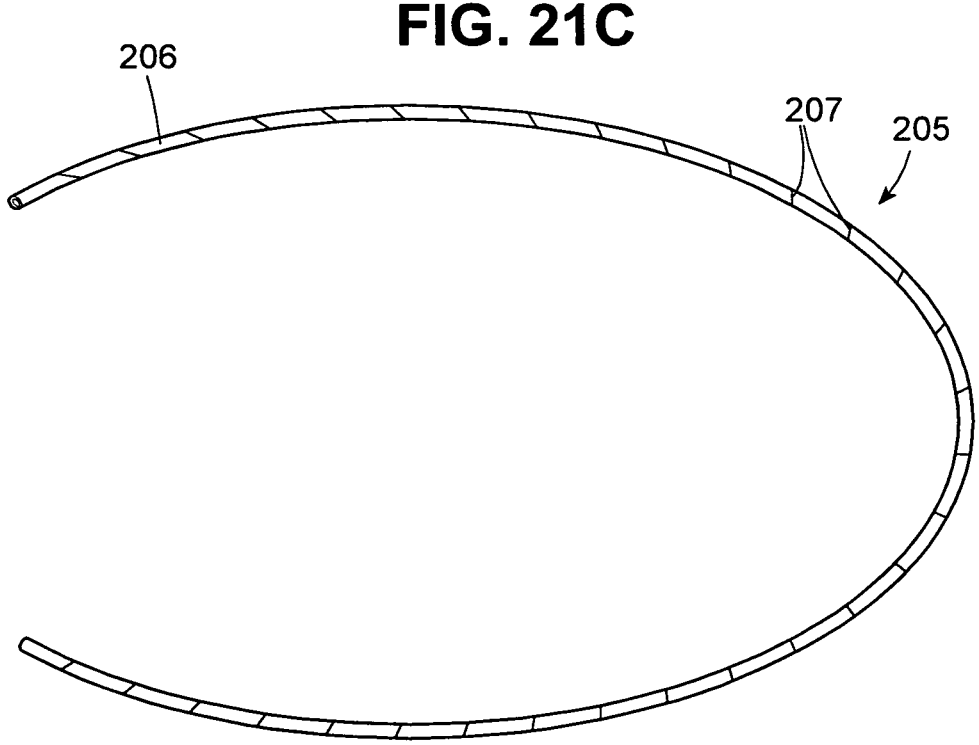

As discussed above in respect of the tubular strip of FIG. 21, the tubes of FIGS. 21B and 21C can have various cross sections. In FIG. 21B, tube 203 of strip 204 can be made from a solid, porous, semi-porous, semi-permeable or woven material and/or it can have holes or slots or slits.

Strip 205 in FIG. 21C is comprised of a tube 206 having a helical slit 207 which runs the entire length of the tube.

Multiple tubes of the kind illustrated and described in respect of FIGS. 21B and 21C can be arranged together. For example, they can be stacked as in FIG. 21 or arranged in rows or combinations of rows and stacks or the like. Combinations of tubes 203 and 206 can also be used in such multiple tube embodiments. Tubes may also be made in a rolled form and bone growth enhancers and/or medications can be incorporated into the rolled tubular strip. These rolled strips may be sufficiently flexible (or soft) such that they readily conform to the size and shape of the kerf when inserted in a patient's skull.

Figure 22:
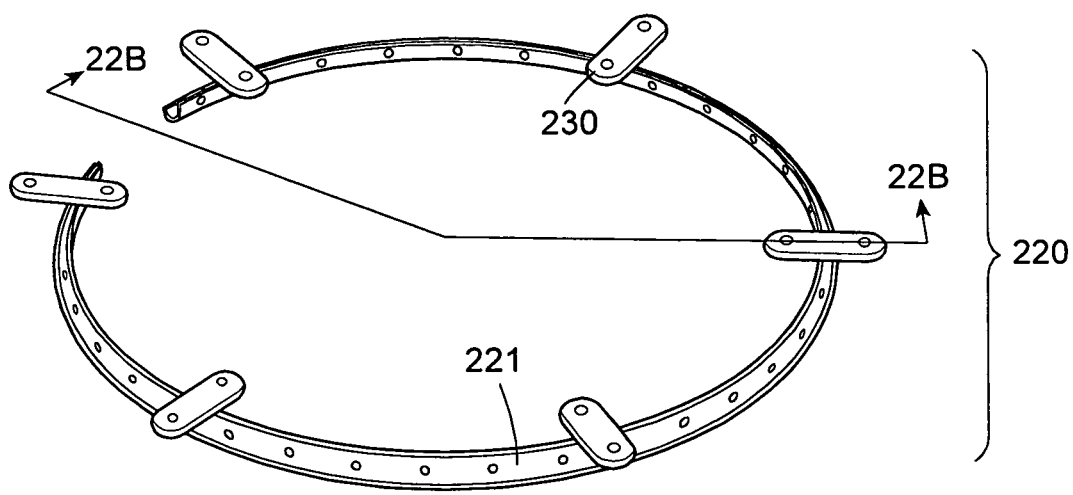
FIG. 22 is a perspective view of fasteners of the invention in combination with a perforated, J-shaped, flexible strip.
Figure 22A:
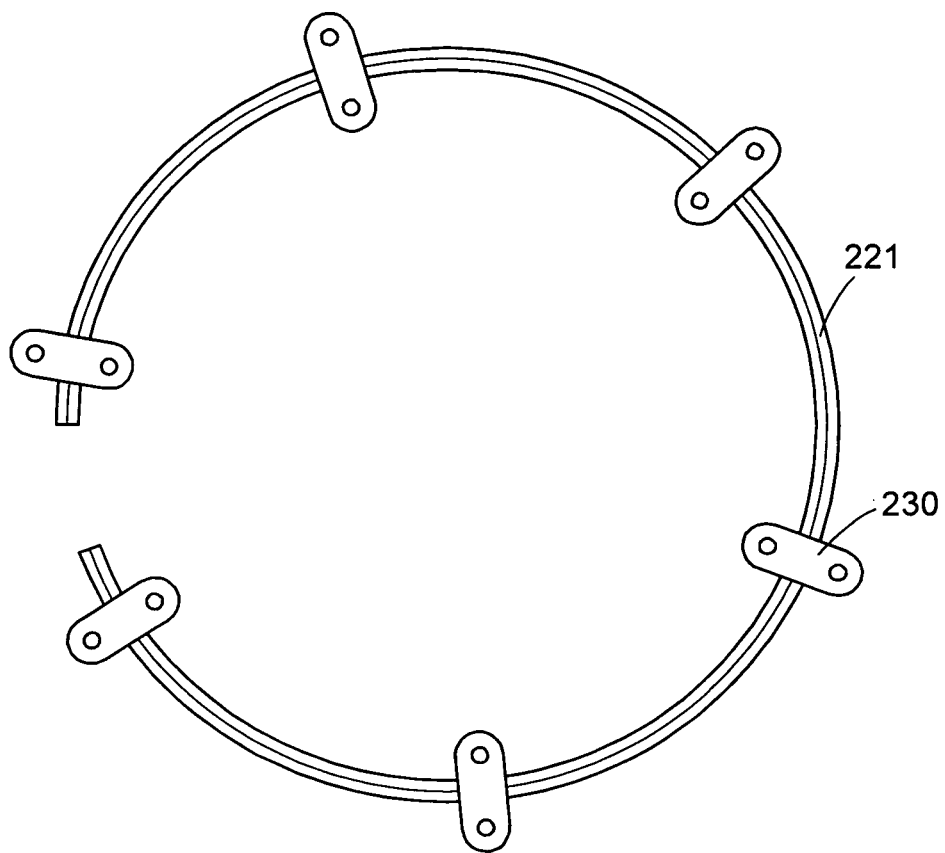
FIG. 22A is a top view and FIG. 22B is a section view of the FIG. 22 embodiment.
Figure 22B:
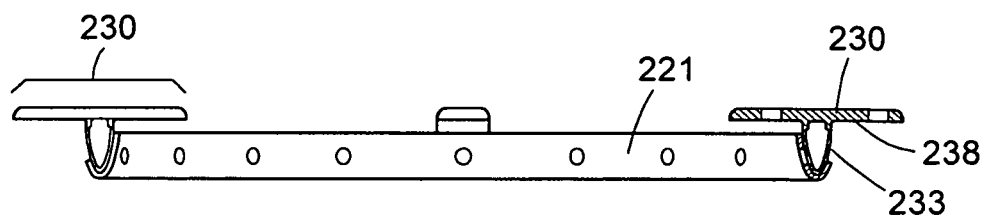

The strip 220 illustrated in FIGS. 22, 22A and 22B is comprised of a J-shaped flexible strip 221 which is pre-curved and sufficiently flexible to be shaped to follow the perimeter contour of a skull flap. This embodiment has been illustrated with fastener 230 which is a slight variant of the fastener 20 as explained in the below discussion of FIG. 23. In this embodiment, the projection 233 purposely positions the J-shaped cavity of the strip 221 below the level of the underside of the flange 231 to insure that the J-shaped flexible strip 221 remains below the top surface of the skull and skull flap. In this embodiment the strip can be affixed to the skull flap before or after the fasteners are affixed to the flap or the strip can be affixed to the fasteners before the fasteners are affixed to the flap. Any strip having an open upper portion such as a U, V, W or J-shaped strip can be used with a fastener having a compatibly shaped projection.

Figure 23:
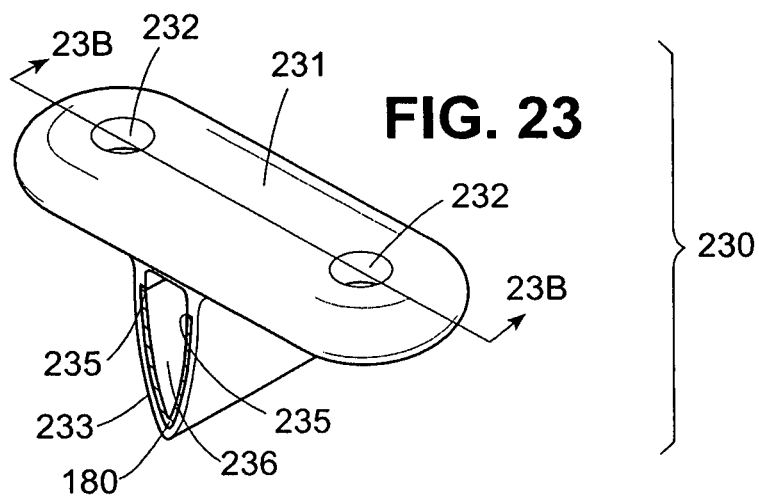
FIG. 23 is a perspective view of a fastener of the invention which can be used in conjunction with various strips.
Figure 23A:
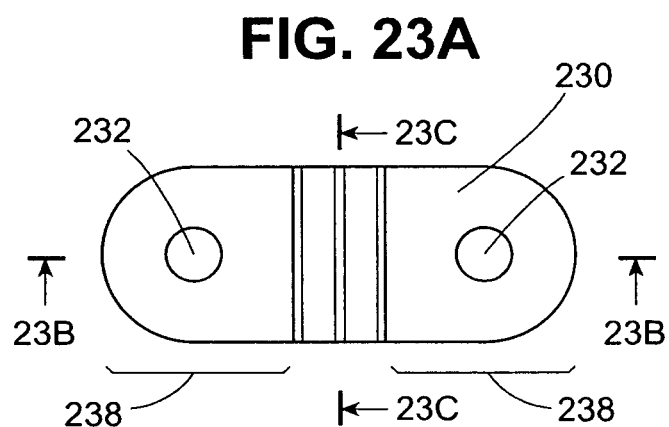
FIG. 23A is a bottom view and FIGS. 23B and C are section views of the FIG. 23 fastener.
Figure 23B:
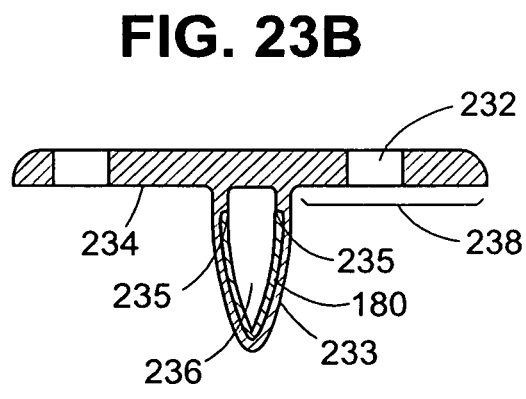
FIGS. 23D and 23E are top views of the FIG. 23 fastener, each illustrating the fastener with a different strip threaded through the aperture.
Figure 23C:
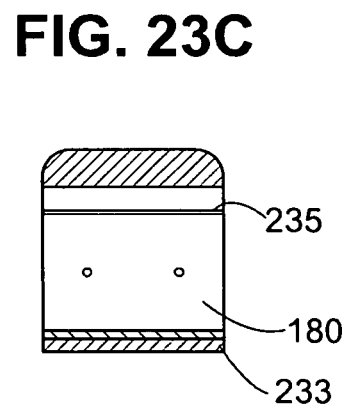
Figure 23D:
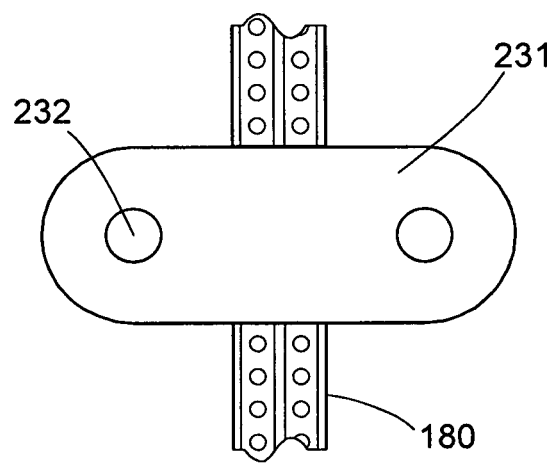
Figure 23E:
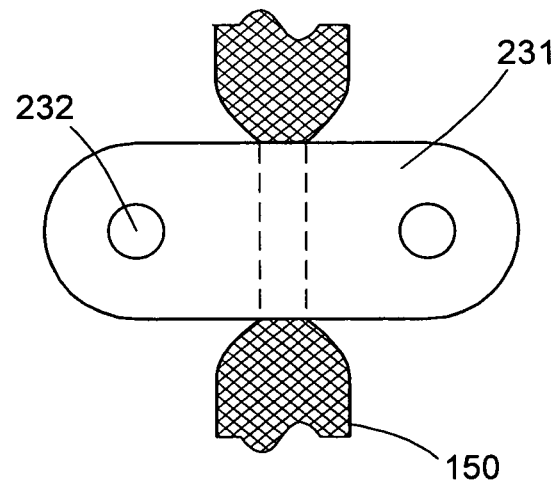

FIG. 23 illustrates a perspective view of a fastener 230 with a continuous elongate flange 231 creating lower surfaces 238 each of which will be affixed to one side of the kerf when the fastener is implanted in a patient. Optional fastener holes 232 are shown in the flange. A V-shaped projection 233 having an aperture 236 projects from the underside 234 of the flange and the aperture is illustrated with a compatibly shaped flexible strip 180. In other words, the strip 180 is threaded through the aperture 236 in the V-shaped projection 233 of fastener 230. FIG. 23A is a view of the underside of FIG. 23, FIG. 23B is a section view taken through the section line 23B-23B of FIG. 23A and FIG. 23C is a section view taken through section line 23C-23C of FIG. 23A. FIG. 23D is a top view of a fastener 230 with a V-shaped strip 180 threaded through the aperture thereof. Of course, strips of many other shapes could be threaded through the aperture as long as they can be pulled through the aperture. A flexible strip such as, for example, a woven strip or a flexible tube can be threaded through the aperture even if the cross-section is wider than the aperture. In that case, it will simply be squeezed within the aperture but allowed to expand to its original size on both sides of the aperture. This is illustrated in FIG. 23E wherein a woven strip 150 has been threaded through the aperture of the fastener and the strip 150 is wider than the aperture.

Optional tabs 235 on the inside of the aperture 236 position the strip 180 at a distance below the underside of the flange 234. The fasteners could be affixed to the strip or could be able to slide along its length. Obviously other strip cross-sections (U, J, W, tubular) could be used in a similar manner.

What is claimed is:

1. A craniotomy closure used to reattach a skull flap removed from a skull during brain surgery, the craniotomy closure comprising:
    a fastener comprising a biocompatible material and having:
        a flange having an upper surface, a lower surface and a central axis, the flange having at least two elongated ends extending away from the central axis of the flange, the two elongated ends each having at least one hole extending through the top surface to the bottom surface; and
        a flexible projection having a width adapted to fit in a kerf and extending downwardly from the lower surface of the flange, the projection having an aperture having a central axis disposed in parallel with the lower surface of the flange, and
    a surgical strip comprising a biocompatible material and having a cross-section in the shape of a V, U, J, W or a tube, wherein the aperture of the flexible projection is shaped to accommodate the surgical strip.

2. The closure of claim 1 comprising at least two fasteners.

3. The closure of claim 1 wherein the surgical strip is configured for threaded engagement through the aperture.

4. The closure of claim 1 wherein the surgical strip is a formable material, a moldable material or a compressible material.

5. The fastener of claim 1 further comprising an opening extending from the upper surface of the flange into the aperture.

6. The closure of claim 1 wherein the surgical strip further comprises a leader affixed to one end thereof.

7. The closure of claim 1 wherein the surgical strip further comprises a leader affixed to both ends thereof.

* * * * *